United States Patent [19]

Togino

[11] Patent Number: 5,912,764
[45] Date of Patent: Jun. 15, 1999

[54] ENDOSCOPE OPTICAL SYSTEM AND IMAGE PICKUP APPARATUS

[75] Inventor: Takayoshi Togino, Koganei, Japan

[73] Assignee: Olympus Optical Co., Ltd., Tokyo, Japan

[21] Appl. No.: 08/816,266

[22] Filed: Mar. 13, 1997

[30] Foreign Application Priority Data

Sep. 18, 1996 [JP] Japan .................................. 8-245871

[51] Int. Cl.$^6$ .......................... A61B 1/055; G02B 3/02; G02B 17/08; G02B 5/04
[52] U.S. Cl. ...................... 359/367; 359/678; 359/708; 359/837; 359/728
[58] Field of Search .......................... 359/367, 678, 359/708, 711, 720, 737, 837, 728, 722, 726; 348/65; 600/170, 171, 176

[56] References Cited

U.S. PATENT DOCUMENTS

| 3,810,221 | 5/1974 | Plummer . | |
|---|---|---|---|
| 3,836,931 | 9/1974 | Plummer . | |
| 4,383,761 | 5/1983 | Jones | 359/367 |
| 5,701,202 | 12/1997 | Takahashi | 359/631 |

FOREIGN PATENT DOCUMENTS

| 722 106 | 7/1996 | European Pat. Off. . |
|---|---|---|
| 62-144127 | 6/1987 | Japan . |
| 62-205546 | 9/1987 | Japan . |
| 62-205547 | 9/1987 | Japan . |

*Primary Examiner*—Jon Henry
*Attorney, Agent, or Firm*—Pillsbury Madison & Sutro LLP

[57] ABSTRACT

A compact endoscope optical system capable of providing a clear image of minimal distortion even at a wide field angle. The endoscope optical system includes an objective optical system for forming an object image. The objective optical system has a prism member (3) having reflecting surfaces (5, 6) for bending an optical path. The endoscope optical system further includes an image transfer system for leading the object image formed by the objective optical system to an observation apparatus along the direction of a major axis. The objective optical system has a configuration producing decentration aberration by bending the optical path. The prism member (3) has at least one curved surface (4 to 7) having an optical action in the optical path. The curved surface is such a non-rotationally symmetric surface having no axis of rotational symmetry in nor out of the surface as to correct the decentration aberration.

24 Claims, 9 Drawing Sheets

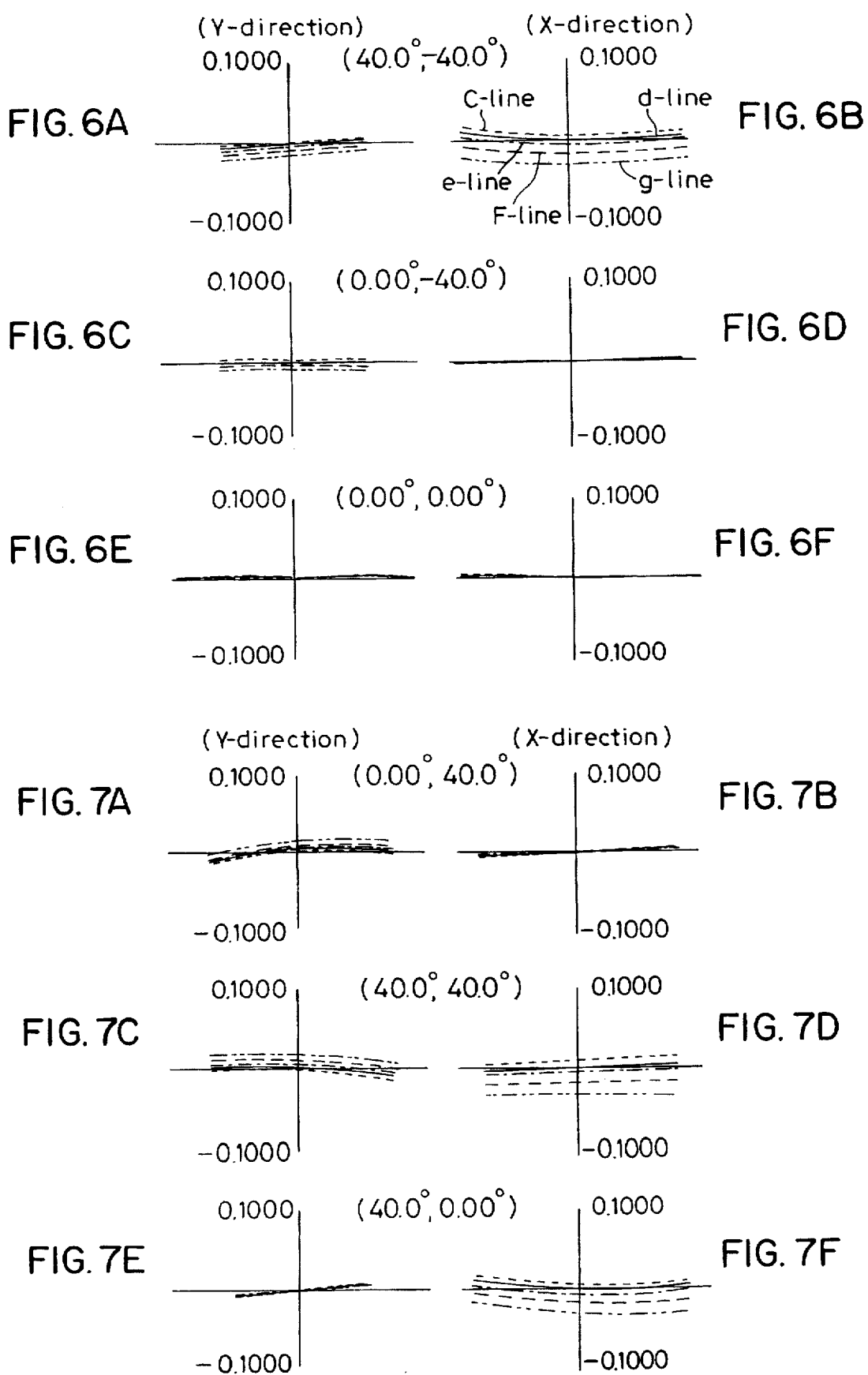

ENDOSCOPE OPTICAL SYSTEM AND IMAGE PICKUP APPARATUS

BACKGROUND OF THE INVENTION

The present invention relates to an endoscope optical system and, more particularly, to an endoscope optical system including an image-forming optical system which has a power and includes a decentered reflecting surface.

There has heretofore been known a compact reflecting decentered optical system as disclosed in Japanese Pat. Appln. Laid-Open (KOKAI) No. 59-84201. This is an invention of a one-dimensional light-receiving lens comprising a cylindrical reflecting surface; therefore, two-dimensional imaging cannot be effected with this conventional optical system. Japanese Pat. Appln. Laid-Open (KOKAI) No. 62-144127 discloses an optical system wherein the identical cylindrical surface is used twice to effect reflection in order to reduce spherical aberration in the above-mentioned invention.

Japanese Pat. Appln. Laid-Open (KOKAI) No. 62-205547 discloses the use of an aspherical reflecting surface as a reflecting surface, but makes no mention of the configuration of the reflecting surface. U.S. Pat. Nos. 3,810,221 and 3,836,931 both disclose an example in which a rotationally symmetric aspherical mirror and a lens system having a surface which has only one plane of symmetry are used to constitute a finder optical system of a reflex camera. In this examples however, the surface having only one plane of symmetry is utilized for the purpose of correcting the tilt of a virtual image for observation.

Japanese Pat. Appln. Laid-Open (KOKAI) No. 1-257834 (U.S. Pat. No. 5,274,406) discloses an example in which a surface having only one plane of symmetry is used for a reflecting mirror to correct image distortion in a back projection type television. In this example, however, a projection lens system is used for projection onto a screen, and the surface having only one plane of symmetry is used for correction of image distortion.

Japanese Pat. Appln. Laid-Open (KOKAI) No. 7-333551 discloses an example of a back-coated mirror type decentered optical system using an anamorphic surface and a toric surface as an observation optical system. However, the decentered optical system is not sufficiently corrected for aberrations, including image distortion.

None of the above-described prior art references uses a surface having only one plane of symmetry as a back-coated mirror to form a turn-back optical path.

In the conventional decentered optical systems, however, an imaged figure or the like is undesirably distorted and the correct shape cannot be recorded unless aberrations of the formed real image are favorably corrected and distortion is favorably corrected.

In a rotationally symmetric optical system comprising a refracting lens which is formed from a surface that is rotationally symmetric about an optical axis, a straight-line optical path is formed. Therefore, the whole optical system is undesirably lengthened in the direction of the optical axis, resulting in an unfavorably large-sized apparatus.

SUMMARY OF THE INVENTION

In view of the problems associated with the prior art, an object of the present invention is to provide a compact endoscope optical system capable of providing a clear image of minimal distortion even at a wide field angle.

To attain the above-described object, the present invention provides an endoscope optical system includes an objective optical system for forming an object image. The objective optical system has a prism member that has at least a reflecting surface for bending an optical path. The endoscope optical system further includes an image transfer system for leading the object image formed by the objective optical system to an observation apparatus along the direction of a major axis. The objective optical system has a configuration producing decentration aberration by bending the optical path. The prism member has at least one curved surface that has an optical action in the optical path. The curved surface is such a non-rotationally symmetric surface having no axis of rotational symmetry in nor out of the surface as to correct the decentration aberration.

In addition, the present invention provides an endoscope optical system that includes an objective optical system for forming an object image. The objective optical system has a prism member having at least a reflecting surface for bending an optical path. The endoscope optical system further includes an image transfer system for leading the object image formed by the objective optical system to an observation apparatus along the direction of a major axis. The reflecting surface of the prism member has a surface configuration producing decentration aberrations and at least one of the reflecting surface and another reflecting surface of the prism member is such a non-rotationally symmetric surface having no axis of rotational symmetry in nor out of the surface as to correct the decentration aberration.

In the above-described endoscope optical systems, it is desirable for the non-rotationally symmetric surface to have a configuration having only one plane of symmetry and defined by the following equation:

$$\begin{aligned}
Z = & C_2 \\
& + C_3 y + C_4 x \\
& + C_5 y^2 + C_6 yx + C_7 x^2 \\
& + C_8 y^3 + C_9 y^2 x + C_{10} yx^2 + C_{11} x^3 \\
& + C_{12} y^4 + C_{13} y^3 x + C_{14} y^2 x^2 + C_{15} yx^3 + C_{16} x^4 \\
& + C_{17} y^5 + C_{18} y^4 x + C_{19} y^3 x^2 + C_{20} y^2 x^3 + C_{21} yx^4 \\
& \quad + C_{22} x^5 \\
& + C_{23} y^6 + C_{24} y^5 x + C_{25} y^4 x^2 + C_{26} y^3 x^3 + C_{27} y^2 x^4 \\
& \quad + C_{28} yx^5 + C_{29} x^6 \\
& + C_{30} y^7 + C_{31} y^6 + C_{32} y^5 x^2 + C_{33} y^4 x^3 + C_{34} y^3 x^4 \\
& \quad + C_{35} y^2 x^5 + C_{36} yx^6 + C_{37} x^7
\end{aligned} \quad (a)$$

where $C_m$ (m is an integer of 2 or higher) are coefficients.

The reason for adopting the above-described arrangements in the present invention, together with the functions thereof, will be explained below.

First of all, a coordinate system used in the following description will be explained, It is assumed that a light ray passing through the center of a stop to reach the center of an image plane is defined as an image center principal ray. It is also assumed that an optical axis defined by a straight line along which the image center principal ray emanating from the stop intersects the first surface of the image-forming optical system is defined as a Z-axis, and that an axis perpendicularly intersecting the Z-axis in the decentration plane of each surface constituting the image-forming optical system is defined as a Y-axis, and further that an axis perpendicularly intersecting both the Z- and Y-axes is defined as an X-axis.

Ray tracing will be described by forward ray tracing in which light rays are traced from the object toward the image plane.

In general, aspherical surfaces are used in order to effect favorable aberration correction with a minimal number of surfaces. Spherical lens systems generally adopt an arrangement in which aberrations produced by a spherical surface, such as spherical aberration, coma, field curvature, etc., are corrected by another surface. In order to reduce various aberrations which would be produced by a spherical surface, an aspherical surface is used. The purpose of using an aspherical surface is to reduce various aberrations which would be produced by one surface and to minimize the number of surfaces used to effect aberration correction, thereby minimizing the number of surfaces constituting the whole optical system.

The above-mentioned Japanese Pat. Appln. Laid-Open (KOKAI) No. 1-257834 uses a Fresnel reflecting surface similar to a three-dimensional surface (three-dimensional polynomial surface) used in the present invention. However, the purpose of using the Fresnel reflecting surface is to correct a trapezoidal image distortion. That is, a real image is projected by a transmission optical system, and only a trapezoidal image distortion is corrected by the reflecting surface.

However, a prism optical system which is decentered and has a small number of constituent elements as in the case of the present invention suffers from aberrations due to decentration which cannot be corrected by a conventionally employed rotationally symmetric aspherical surface. Aberrations due to decentration include coma, astigmatism, image distortions field curvature, etc. There are conventional design examples in which a toric surface, an anamorphic surface, etc. are used to correct such aberrations. However, there has heretofore been proposed no device which is designed with great importance placed on the correction of astigmatism caused by decentration, and which is compact and provides a wide field angle, and further which is satisfactorily corrected for aberrations.

The present invention is characterized by using a three-dimensional surface as a reflecting surface which corrects the above-described aberrations simultaneously and favorably and which has all the refracting power of the optical system.

The term "three-dimensional surface" as used in the present invention means a surface which is defined by the following equation:

$$Z = C_2 \quad (a)$$
$$+ C_3 y + C_4 x$$
$$+ C_5 y^2 + C_6 yx + C_7 x^2$$
$$+ C_8 y^3 + C_9 y^2 x + C_{10} yx^2 + C_{11} x^3$$
$$+ C_{12} y^4 + C_{13} y^3 x + C_{14} y^2 x^2 + C_{15} yx^3 + C_{16} x^4$$
$$+ C_{17} y^5 + C_{18} y^4 x + C_{19} y^3 x^2 + C_{20} y^2 x^3 + C_{21} yx^4$$
$$+ C_{22} x^5$$
$$+ C_{23} y^6 + C_{24} y^5 x + C_{25} y^4 x^2 + C_{26} y^3 x^3 + C_{27} y^2 x^4$$
$$+ C_{28} yx^5 + C_{29} x^6$$
$$+ C_{30} y^7 + C_{31} y^6 + C_{32} y^5 x^2 + C_{33} y^4 x^3 + C_{34} y^3 x^4$$
$$+ C_{35} y^2 x^5 + C_{36} yx^6 + C_{37} x^7$$

where $C_m$ (m is an integer of 2 or higher) are coefficients.

The reason for using the above-described three-dimensional surface in the present invention will be explained below in detail.

First, rotationally asymmetric field curvature produced by a decentered concave mirror will be described. For example, when light rays from an infinitely distant object point are incident on the concave mirror, the light rays are reflected by the concave mirror. The distance to the image surface from a point on which a light ray impinges is a half of the curvature at the portion on which the light ray impinges. That is, the light rays form an image surface which is tilted with respect to the direction of travel of light rays having been reflected from the decentered concave mirror. Using a three-dimensional surface according to the present invention makes it possible to give desired curvatures in the X- and Y-axis directions at any point relative to the positive and negative directions of the Y-axis. This is because, as will be clear from the defining equation (a), the three-dimensional surface has terms with odd-numbered powers of y which enable the curvature to be varied as desired according to the sign (positive or negative) of the Y-axis. This is effective in correcting a rotationally asymmetric field curvature, particularly the tilt of the image surface, produced by a decentered concave mirror.

Next, rotationally asymmetric field curvature will be explained. In general, a reflecting mirror produces curvature of field along the reflecting surface. The image-forming optical systems according to the present invention are generally arranged such that the field curvature can be corrected by a convex mirror which pairs with a concave mirror as described above. However, the field curvature cannot be completely corrected because the number of surfaces is small. It is preferable in order to correct the field curvature left uncorrected to use a three-dimensional surface according to the present invention, which enables a desired curvature to be given at any position.

Astigmatism can be corrected by appropriately changing the difference between the curvature in the X-axis direction and the curvature in the Y-axis direction.

In view of the productivity of optical parts, it is even more desirable to minimize the number of three-dimensional surfaces used. Accordingly, it is preferable to use the above-described three-dimensional surface as one reflecting surface of the prism optical system and a plane surface or a spherical surface or a decentered rotationally symmetric surface as each of the remaining surfaces. By doing so, it is possible to improve the productivity.

In the present invention, the above-described three-dimensional surface is used as at least one reflecting surface having reflecting action, and the surface configuration of the reflecting surface is defined as a plane-symmetry three-dimensional surface which has no axis of rotational symmetry, and which has only one plane of symmetry. More specifically, when a coordinate system is set as shown for example in FIGS. 10(a) and 10(b), the reflecting surface is formed as a three-dimensional surface having a plane of symmetry lying in the YZ-plane, which is a plane containing the direction of decentration of the decentered surface. By doing so, the image formed in the image plane can be made symmetric with respect to the YZ-plane as a plane of symmetry. Thus, the cost for aberration correction can be reduced to a considerable extent.

It should be noted that the term "reflecting surface having reflecting action" as used in the present invention includes any reflecting surface having reflecting action, e.g. a totally reflecting surface, a mirror-coated surface, a semitransparent reflecting surface, etc.

One image-forming optical system according to the present invention has a prism optical system having a prism formed from at least two curved surfaces, and an image pickup device disposed at an image-formation position of the prism optical system. The two curved surfaces include a first reflecting surface disposed at a tilt to face an object point, and a second reflecting surface tilted with respect to both the first reflecting surface and an image plane. The image-forming optical system is arranged such that light rays from the object point travel along an optical axis and are reflected by the first reflecting surface of the prism optical system toward a side opposite to the image plane with respect to the optical axis and then reflected by the second reflecting surface to reach the image plane by substantially intersecting the optical axis. At least one of the first and second reflecting surfaces is a non-rotationally symmetric surface having no axis of rotational symmetry, neither one that intersects the surface nor one that is completely outside of the surface.

Another image-forming optical system according to the present invention has a prism optical system having a prism formed from at least two curved surfaces, and an image pickup device disposed at an image-formation position of the prism optical system The two curved surfaces include a first reflecting surface disposed at a tilt to face an object point, and a second reflecting surface tilted with respect to both the first reflecting surface and an image plane. The image-forming optical system is arranged such that light rays from the object point travel along an optical axis and are reflected by the first reflecting surface of the prism optical system toward the image plane with respect to the optical axis and then reflected by the second reflecting surface to reach the image plane without intersecting the optical axis. At least one of the first and second reflecting surfaces is a non-rotationally symmetric surface having no axis of rotational symmetry in nor out of the surface.

In these image-forming optical systems, an image-forming action is given to the prism optical system for folding and also bending the optical path. Accordingly, the prism optical system has both the optical path bending action and image-forming action. Therefore, it is possible to simplify the arrangement and to reduce the overall size of the system.

It is desirable to satisfy the following condition f<20 millimeters where f is a focal length defined by a value obtained by dividing the ray height of a bundle of parallel rays incident on the prism optical system from the object side thereof by the numerical aperture on the image side thereof.

The above condition shortens the focal length to form the prism optical system in a compact structure. In the conventional optical systems, a reduction of the focal length causes an increase in the number of constituent lens elements in order to correct aberrations. Therefore, it has heretofore been difficult to form a compact optical system. However, it becomes possible to shorten the focal length by forming at least one of the first and second reflecting surfaces from a non-rotationally symmetric surface having no axis of rotational symmetry, neither intersecting the surface nor completely outside of the surface.

An optical system may be provided between the object point and the above-described prism optical system. That is, in addition to the prism optical system having a three-dimensional surface, an optical system may be disposed on the object side of the prism optical system. By doing so, it becomes possible to increase the degree of freedom for aberration correction. If an optical system having a negative refracting power is used as the object-side optical system to increase the field angle, a wide field angle can be obtained. By providing a negative optical system on the object side of the prism optical system, it is possible to converge light rays from the object over a wide field angle as they are incident on the prism optical system. Thus, it becomes possible to widen the field angle without increasing the size of the prism optical system.

In a case where the negative optical system is formed from a lens having a negative refracting powers the negative lens produces a large amount of image distortion and lateral chromatic aberration. Therefore, it is preferable with a view to effecting favorable aberration correction to arrange the system such that the aberrations produced by the negative lens and the aberrations produced by the prism optical system cancel each other.

It is preferable from the viewpoint of minimizing image distortion produced by the negative lens that the radius of curvature on the prism optical system side of the negative lens should be smaller than the radius of curvature on the object side of the negative lens.

If a rotationally symmetric surface is used to constitute the negative lens, the productivity of the lens improves.

The negative lens may be formed from a rotationally asymmetric surface. In this case, it is possible to correct image distortion even more favorably.

If the negative lens is produced in the form of a diffraction optical element or a Fresnel lens, it can be formed as a thin lens. This is effective when it is desired to construct a compact optical system.

It is also possible to provide an optical system between the prism optical system and the image-formation position. By doing so, the degree of freedom for aberration correction can be increased. If the added optical system has a positive refracting power, the prism optical system can be made compact while favorably maintaining the telecentricity on the image side. More specifically, if an optical system having a positive refracting power is disposed between the prism optical system and the image-formation position, it is possible to set the pupil position of the optical system in the prism optical system and to dispose the exit pupil at a distant place. Thus, it becomes possible to make the prism optical system compact while maintaining the telecentricity on the image side. If the optical element that has a positive refracting power is not used, the telecentricity is degraded. When a CCD, for example, is used as an image pickup device, the light-gathering efficiency is reduced. When an image guide is used, the light-gathering efficiency is reduced to such an extent that it becomes impossible to observe a bright image unless an optical fiber bundle of large numerical aperture is used.

In a case where the positive optical system is formed from a lens having a positive refracting power, the positive lens produces a large amount of image distortion and lateral chromatic aberration. Therefore, it is preferable with a view to effecting favorable aberration correction to arrange the system such that the aberrations produced by the positive lens and the aberrations produced by the prism optical system cancel each other.

It is preferable from the viewpoint of minimizing image distortion produced by the positive lens that the radius of curvature on the image plane side of the positive lens should be smaller than the radius of curvature on the object side of the positive lens.

The positive lens may be arranged such that a curvature is given to the object side of the positive lens, and the image plane side of the positive lens has a flat surface and is integrated with the image pickup device. By doing so, the productivity can be improved.

If a rotationally symmetric surface is used to constitute the positive lens, the productivity of the lens improves.

The positive lens may be formed from a rotationally asymmetric surface. In this case, it is possible to correct image distortion even more favorably.

If the positive lens is produced in the form of a diffraction optical element or a Fresnel lens, it can be formed as a thin lens. This is effective when it is desired to construct a compact optical system.

The use of the above-described prism optical system enables a compact endoscope optical system to be realized.

When a plane-symmetry three-dimensional surface which has only one plane of symmetry is used as at least one reflecting surface of an image-forming optical system as described above, it is possible to provide an image-forming optical system having a wide field angle and favorably corrected for aberrations by satisfying the following conditions.

First, when X- Y- and Z-axes are determined according to the above definition, a light ray which emanates from the center of the object and passes through the center of the aperture to be incident on the center of the image plane is defined as an axial principal ray, and four portions in the effective area of each reflecting surface are determined by combinations of field angles in the directions X and Y, i.e. the field angle zero in the direction X, the maximum field angle in the direction X, the maximum field angle in the direction +Y, the field angle zero in the direction Y, and the maximum field angle in the direction -Y, as shown in Table 1 below:

TABLE 1

|  | Field angle zero in direction X | Maximum field angle in direction X |
| --- | --- | --- |
| Maximum field angle in direction +Y | ① | |
| Field angle zero in direction Y | ② | ⑤ |
| Maximum field angle in direction -Y | ③ | |

As shown in Table 1: a portion on which the axial principal ray impinges is defined as ②; an upper portion in the effective area at the maximum vertical field angle is defined as ①; a portion in the effective area at the maximum horizontal field angle is defined as ⑤; and a lower portion in the effective area at the maximum vertical field angle is defined as ③. An equation which defines the configuration of each particular surface in the effective area [i.e. an expression in which the Z-axis is expressed as an axis of the surface, or an expression in which the surface is expressed in the form of Z=f(X,Y) on the assumption that the surface is not decentered] is solved to determine the tilts of the surface at the portions ① to ③ and ⑤ in the Y-axis direction, which corresponds to the decentering direction of the surface. The tilts are denoted by DY1 to DY3 and DY5, and the curvatures at the portions ① to ③ and ⑤ are denoted by CY1 to CY3 and CY5. The tilts of the surface at the portions ① to ③ and ⑤ in the X-axis direction, which perpendicularly intersects the Y-axis directions are denoted by DX1 to DX3 and DX5, and the curvatures at these portions are denoted by CX1 to CX3 and CX5.

First, examples of prism optical systems (decentered prisms) having decentered surfaces according to the present invention will be described. FIGS. 10(a) and 10(b) show prism optical systems used in examples (described later). The prism optical system 3 shown in FIG. 10(a) has a first transmitting surface 4, a first reflecting surface 5, a second reflecting surface 6, and a second transmitting surface 7. Light rays from the object point travel along an optical axis 2 and enters the prism optical system 3 through the first transmitting surface 4. The light rays are reflected by the first reflecting surface 5 toward a side opposite to the image plane with respect to the optical axis 2 and then reflected by the second reflecting surface 6. The reflected light rays substantially intersect the optical axis 2 and exit from the prism optical system 3 through the second transmitting surface 7 to reach the image plane. Assuming the intersection between the first transmitting surface 4 and the optical axis 2 to be the origin, the direction of the optical axis 2 is defined as a Z-axis direction, and a direction perpendicularly intersecting the Z-axis and passing through the origin in a plane in which the light rays are bent by the prism optical system 3 is defined as a Y-axis direction. Further, a direction perpendicularly intersecting both the Z- and Y-axes and passing through the origin is defined as an X-axis direction. The direction of travel of the axial principal ray passing through the origin is defined as the positive direction of the Z-axis, and the direction opposite to the image plane with respect to the optical axis 2 is defined as the positive direction of the Y-axis. Further, a direction in which the X-axis constitutes a right-handed system in combination with the Z- and Y-axes is defined as the positive direction of the X-axis.

The prism optical system 3 shown in FIG. 10(b) has a first transmitting surface 4, a first reflecting surface 5, and a second transmitting surface 7. The first transmitting surface 4 also serves as a second reflecting surface 6. Light rays from the object point travel along an optical axis 2 and enter the prism optical system 3 through the first transmitting surface 4. The light rays are reflected by the first reflecting surface 5 toward the image plane side with respect to the optical axis 2 and then reflected by the second reflecting surface 6, which is the first transmitting surface 4 serving as both transmitting and reflecting surfaces. The reflected light rays exit from the prism optical system 3 through the second transmitting surface 7 without intersecting the optical axis 2 and reach the image plane. Assuming the intersection between the first transmitting surface 4 and the optical axis 2 to be the origin, the direction of the optical axis 2 is defined as a Z-axis direction, and a direction perpendicularly intersecting the Z-axis and passing through the origin in a plane in which the light rays are bent by the prism optical system 3 is defined as a Y-axis direction. Further, a direction perpendicularly intersecting both the Z- and Y-axes and passing through the origin is defined as an X-axis direction. The direction of travel of the axial principal ray passing through the origin is defined as the positive direction of the Z-axis, and the direction opposite to the image plane with respect to the optical axis 2 is defined as the positive direction of the Y-axis. Further, a direction in which the X-axis constitutes a right-handed system in combination with the Z- and Y-axes is defined as the positive direction of the X-axis.

It is desirable for at least one surface of the prism optical system to satisfy the following condition:

$$-100 < CX2/CY2 < 0 \qquad (1\text{-}1)$$

where, assuming the Y-axis direction to be a vertical direction, CX2 is a curvature of the equation defining the configuration of the surface concerned at a portion at which an axial principal ray emanating from the center of the object in the Z-axis direction intersects the surface, in a plane containing both the X-axis, which is perpendicular to the decentering direction of the surface, and a line normal to the surface, and CY2 is a curvature at the above-described portion of the surface in a plane containing both the Y-axis, which is parallel to the decentering direction, and a line normal to the surface.

The condition (1-1) is necessary to satisfy in order to reduce astigmatism produced by a decentered reflecting surface. In the case of a spherical surface, CX2/CY2=1. However, a decentered spherical surface produces a large amount of aberration such as image distortion, astigmatism, and coma. Therefore, if a decentered surface is formed by using only a spherical surface, it is difficult to correct astigmatism on the optical axis, and the residual astigmatism makes it difficult to view a clear observation image even at the center of the visual field. If CX2/CY2 is not larger than the lower limit of the condition (1-1), i.e. −100, excessively large astigmatism is produced for correcting astigmatism produced by the reflecting surface, and it becomes impossible to satisfactorily correct the astigmatism by another surface. If CX2/CY2 is not smaller than the upper limit of the condition (1-1), i.e. 0, the astigmatism is undercorrected, and some astigmatism remains uncorrected in the optical system as a whole. Only when at least one reflecting surface satisfying the condition (1-1) is provided, it becomes possible to view an observation image having no astigmatism even on the optical axis.

It is preferable to dispose a surface satisfying the condition (1-1) in combination with a surface satisfying either of the following conditions:

$$0 < CX2/CY2 < 1 \quad (1\text{-}2)$$

$$1 < CX2/CY2 < 100 \quad (1\text{-}3)$$

If CX2/CY2 is not larger than the lower limit of the condition (1-2), i.e. 0, the image-formation position of light rays in the XZ-plane becomes excessively distant from the image-formation position of light rays in the YZ-plane, causing astigmatism to occur to a considerable extent. If CX2/CY2 is not smaller than the upper limit of the condition (1-3), the image-formation position of light rays in the YZ-plane becomes excessively distant from the image-formation position of light rays in the XZ-plane, causing astigmatism to occur to a considerable extent in reverse relation to the above. In a case where CX2/CY2=0, astigmatism itself reduces, but it is impossible to correct both astigmatism and coma or other aberration with good balance. Accordingly, a favorable result cannot be obtained.

In optical systems according to Examples 1 and 2 (described later) of the present invention, it is important that both the first and second transmitting surfaces should satisfy the condition (1-1). That is, it is important for the two transmitting surfaces to satisfy the condition (1-1) in order to make aberration correction such that field curvature and coma produced by the second reflecting surface and field curvature and coma produced by the first transmitting and first reflecting surfaces cancel each other with good balance.

Next, the focal length of each surface of the decentered prism will be described. Let us assume that a light ray having a height of 0.01 millimeter in the X-direction and parallel to the optical axis is made incident on the whole optical system from the object side thereof, and an angle formed in the X-axis direction by the light ray exiting from the image plane side of the optical system with the axial principal ray is a numerical aperture $NA_i$, and that $0.01/NA_i$ is a focal length FX in the X-axis directions and the focal length in the X-axis direction of a portion struck by the axial principal ray, which is obtained from the configuration of each surface, is FX2. In the optical systems according to Examples 1 and 2 (described later) of the present invention, it is preferable from the viewpoint of aberration correction for all the surfaces to satisfy the following condition:

$$-2 < FX/FX2 < 2 \quad (2\text{-}1)$$

If FX/FX2 is not larger than the lower limit of the condition (2-1), i.e. −2, or not smaller than the upper limits i.e. 2, the focal length distribution over the surface is deviated. Consequently, aberrations produced by a surface having a strong refracting power become impossible to correct by another surface. In particular, if FX/FX2 is not larger than the lower limit of the condition (2-1), the negative power becomes excessively strong, and it becomes impossible to form an optical system having a positive power as a whole. If FX/FX2 is not smaller than the upper limit of the condition (2-1), the positive power becomes excessively strong, and strong positive curvature of field occurs, which cannot be corrected by another surface.

It is even more desirable from the viewpoint of aberration correction to satisfy the following condition:

$$-1 < FX/FX2 < 1 \quad (2\text{-}2)$$

Next, in optical systems according to Examples 4 and 5 (described later) of the present invention, it is preferable from the viewpoint of aberration correction that the first reflecting surface of the prism optical system should satisfy the following condition:

$$0 < FX/FX2 < 10 \quad (2\text{-}3)$$

If FX/FX2 is not larger than the lower limit of the condition (2-3), i.e. 0, the power of the second reflecting surface, which is concave toward the stop, becomes weak, and comatic aberration becomes large and impossible to correct by another surfaces. If FX/FX2 is not smaller than the upper limit of the condition (2-3), i.e. 10, the same problem as in the case of the condition (2-1) arises.

It is even more desirable from the viewpoint of aberration correction to satisfy the following condition:

$$0.2 < FX/FX2 < 5 \quad (2\text{-}4)$$

In the optical systems according to Examples 3 to 5 (described later) of the present invention, it is preferable from the viewpoint of aberration correction that the second reflecting surface of the prism optical system should satisfy the following condition:

$$-10 < FX/FX2 < 0 \quad (2\text{-}5)$$

If FX/FX2 is not smaller than the upper limit of the condition (2-5), i.e. 0, field curvature produced by the first reflecting surface cannot effectively be corrected by the second reflecting surface. Consequently, field curvature which is convex in the center thereof occurs to a considerable extent. The meaning of the lower limit, i.e. −10, is the same as that of the lower limit of the condition (2-1).

It is even more desirable from the viewpoint of correcting field curvature to satisfy the following condition:

$$-1 < FX/FX2 < 0 \quad (2\text{-}6)$$

In the optical systems according to Examples 3 to 5 (described later) of the present invention, it is preferable from the viewpoint of aberration correction that the second transmitting surface of the prism optical system should satisfy the following condition:

$$0<FX/FX2<100 \quad (2\text{-}7)$$

If FX/FX2 is not larger than the lower limit of the condition (2-7), i.e. 0, the balance of chromatic aberrations produced in front of and behind the stop is destroyed, and it becomes impossible to correct the chromatic aberrations. If FX/FX2 is not smaller than the upper limit of the condition (2-7), i.e. 100, the positive power of this surface becomes close to 0, and chromatic aberrations produced by another surface become excessively large.

It is even more desirable from the viewpoint of aberration correction to satisfy the following condition:

$$0.5<FX/FX2<100 \quad (2\text{-}8)$$

It is still more desirable from the viewpoint of aberration correction to satisfy the following condition:

$$1<FX/FX2<100 \quad (2\text{-}9)$$

Similarly, the power in the Y-axis direction of each surface will be described below.

Let us assume that a light ray having a height of 0.01 millimeter in the Y-axis direction and parallel to the optical axis is made incident on the whole optical system from the object side thereof, and an angle formed in the Y-axis direction by the light ray exiting from the image plane side of the optical system with the axial principal ray is a numerical aperture $NA_i$, and that $0.01/NA_i$ is a focal length FY in the Y-axis direction, and the focal length in the Y-axis direction of a portion struck by the axial principal ray, which is obtained from the configuration of each surface, is FY2. It is preferable from the viewpoint of aberration correction for all the surfaces to satisfy the following condition:

$$-1<FY/FY2<5 \quad (3\text{-}1)$$

If FY/FY2 is not smaller than the upper limit of the condition (3-1), i.e. 5, or not larger than the lower limit, i.e. −1, the focal length distribution over the surface is deviated, and aberrations produced by a surface having a strong refracting power become impossible to correct by another surface.

In the optical systems according to Examples 1 and 2 (described later) of the present invention, it is even more desirable from the viewpoint of aberration correction that the first reflecting surface should satisfy the following condition:

$$0<FY/FY2<5 \quad (3\text{-}2)$$

The condition (3-2) specifies the relationship between the power of the first reflecting surface and the power of the second reflecting surface. In an optical system arranged to bend the axial principal ray at about 45° by each reflection as in Examples 1 and 2, it is important to satisfy the condition (3-2) in order to correct curvature of field in the Y-axis direction. If FY/FY2 is not smaller than the upper limit of the condition (3-2), i.e. 5, it becomes impossible for the first reflecting surface to produce sufficiently large field curvature which is concave in the center thereof to correct field curvature produced by the second reflecting surface, which is convex in the center thereof. Consequently, the convex field curvature is under-corrected.

It is preferable from the viewpoint of aberration correction that the second reflecting surface should satisfy the following condition:

$$0<FY/FY2<100 \quad (3\text{-}3)$$

If FY/FY2 is not larger than the lower limit of the condition (3-3), i.e. 0, the second reflecting surface produces excessively large field curvature which is convex in the center thereof, and if the field curvature is corrected by field curvature produced by the first reflecting surface, which is concave in the center thereof, over correction results. If FY/FY2 is not smaller than the upper limit of the condition (3-3), i.e. 100, the positive power of the second reflecting surface becomes excessively small, and chromatic aberrations produced by another surface become excessively large.

It is even more desirable to satisfy the following condition:

$$1<FY/FY2<3 \quad (3\text{-}4)$$

By satisfying the condition (3-4), it is possible to correct aberrations favorably at a wider field angle.

Next, in the optical systems according to Examples 3 to 5 (described later) of the present invention, it is preferable from the viewpoint of aberration correction that the first reflecting surface of the optical system should satisfy the following condition:

$$-0.5<FY/FY2<10 \quad (3\text{-}5)$$

If FY/FY2 is not larger than the lower limit of the condition (3-5), i.e. −0.5, the power of the concave surface becomes excessively strong, and strong positive comatic aberration occurs. If FY/FY2 is not smaller than the upper limit of the condition (3-5), i.e. 10, the power of the second reflecting surface, which is concave toward the stop, becomes weak, and negative comatic aberration becomes strong and impossible to correct by another surface.

It is even more desirable from the viewpoint of aberration correction to satisfy the following condition:

$$0.2<FY/FY2<10 \quad (3\text{-}6)$$

In the optical systems according to Examples 3 to 5 (described later) of the present invention, it is preferable from the viewpoint of aberration correction that all the reflecting surfaces should satisfy the following condition:

$$0<FY/FY2<2 \quad (3\text{-}7)$$

If FY/FY2 is not larger than the lower limit of the condition (3-7), i.e. 0, or not smaller than the upper limit of the condition (3-7), i.e. 2, the power to be shared among the surfaces is assigned to one reflecting surface in regard to the Y-axis direction. Accordingly, astigmatism and comatic aberration produced by the decentered reflecting surface become large and impossible to correct by another surface.

Next, a condition for minimizing an asymmetric image distortion due to decentration will be described. By satisfying the following condition, it is possible to reduce a bow-shaped image distortion in which a horizontal straight line is imaged in the form of a bow-shaped line, and also comatic aberration which occurs even on the optical axis. That is, it is preferable from the viewpoint of aberration correction that at least one surface should satisfy the following condition:

$$0.001<|DY|<10 \quad (4\text{-}1)$$

where DY is a difference between DY5 and DY2 which are the tilts of an equation defining the surface at the portion ② struck by the axial principal ray and the right-hand edge portion ⑤ in the effective area in the Y-axis direction, which corresponds to the decentering direction of the surface, and that a Z-axis is defined such that light rays are incident on the surface from the negative direction of the Z-axis of the surface-defining equation and reflected to travel in the negative direction of the Z-axis.

If |DY| is not larger than the lower limit of the above condition (4-1), i.e. 0.001, the tilt in the Y-axis direction of the center of the right-hand portion in the effective area becomes inappropriate, and it becomes difficult for this surface to correct a bow-shaped image distortion produced by a tilted reflecting surface and axial comatic aberration. If |DY| is not smaller than the upper limit of the condition (4-1), i.e. 10, the produced image distortion becomes excessively large, resulting in over correction.

It is even more desirable for the second transmitting surface to satisfy the above condition (4-1). If the second transmitting surface satisfies the condition (4-1), it is possible to obtain favorable results in terms of aberration correction.

Next, in an optical system arranged to bend the optical axis upwardly by the first reflecting surface as in Examples 1 and 2 (described later), it is important to satisfy the condition described below. It is an important condition for correcting all aberrations, with good balance, which are produced by a decentered surface having only one plane of symmetry, and also for minimizing the tilt of the image plane. This condition is particularly important in an optical system having two decentered concave mirrors as in the present invention.

It is preferable from the viewpoint of aberration correction to satisfy the following condition:

$$0 < CX3-1 < 0.1 \tag{5-1}$$

where CX3-1 denotes CX3-CX1, i.e. a difference between the curvatures CX1 and CX3 in the X-axis direction at the portions ① and ③ in the effective area of a reflecting surface of the optical system.

If CX3-1 is not smaller than the upper limit of the condition (5-1), i.e. 0.1, or not larger than the lower limit of the condition (5-1), i.e. 0, the curvatures in the X-axis direction of the surface at the two portions in the effective area become excessively different from each other, causing higher-order comatic aberrations to occur.

In an optical system arranged to bend the optical axis downwardly as in Examples 3 to 5 (described later), it is even more desirable to satisfy the following condition:

$$-0.1 < CX3 - < 0 \tag{5-2}$$

It is still more desirable from the viewpoint of aberration correction that the second reflecting surface should satisfy the condition (5-2) when the first reflecting surface satisfies the condition (5-1). Similarly, it is preferable for the second reflecting surface to satisfy the condition (5-1) when the first reflecting surface satisfies the condition (5-2).

Next, in an optical system arranged to bend the optical axis upwardly by the first reflecting surface as in Examples 1 and 2 (described later), it is important to satisfy the condition described below. It is an important condition for correcting all aberrations, with good balances which are produced by a decentered surface having only one plane of symmetry, and also for minimizing the tilt of the image plane. This condition is particularly important in an optical system having two decentered concave mirrors as in the present invention.

It is preferable from the viewpoint of aberration correction to satisfy the following condition:

$$-0.3 < CY3-1 < 0.2 \tag{6-1}$$

where CY3-1 denotes CY3-CY1, i.e. a difference between the curvatures CY1 and CY3 in the Y-axis direction at the portions ① and ③ in the effective area of a reflecting surface of the optical system.

If CY3-1 is not smaller than the upper limit of the condition (6-1), i.e. 0.2, or not larger than the lower limit of the condition (6-1), i.e. -0.3, the curvatures in the Y-axis direction of the surface at the two portions in the effective area become excessively different from each other, causing higher-order comatic aberrations to occur. However, if all the surfaces are 0 in terms of CY3-1, it is impossible to correct the tilt of the image plane and comatic aberrations.

In an optical system arranged to bend the optical axis downwardly as in Examples 3 to 5 (described later), it is even more desirable to satisfy the following condition:

$$-0.2 < CY3-1 < 0.1 \tag{6-2}$$

Regarding the above conditions (1-1) to (6-2), it is desirable to satisfy any one of them. By combining two or more of the conditions (1-1) to (6-2), an even more desirable prism optical system can be obtained. The importance ranking of the above conditions, from highest to lowest, is (1-1)–(1-3), (2-1)–(2-9), (3-1)–(3-7), and (4-1).

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIGS. 6A–6F are one part of an aberrational diagram illustrating lateral aberrations in the optical system according to Example 1 of the present invention.

FIGS. 7A–7F are the other part of the aberrational diagram illustrating lateral aberrations in the optical system according to Example 1 of the present invention.

DESCRIPTION OF THE PREFERRED EMBODIMENTS

Examples 1 to 5 of the image-forming optical system according to the present invention will be described below.

Figure 1:
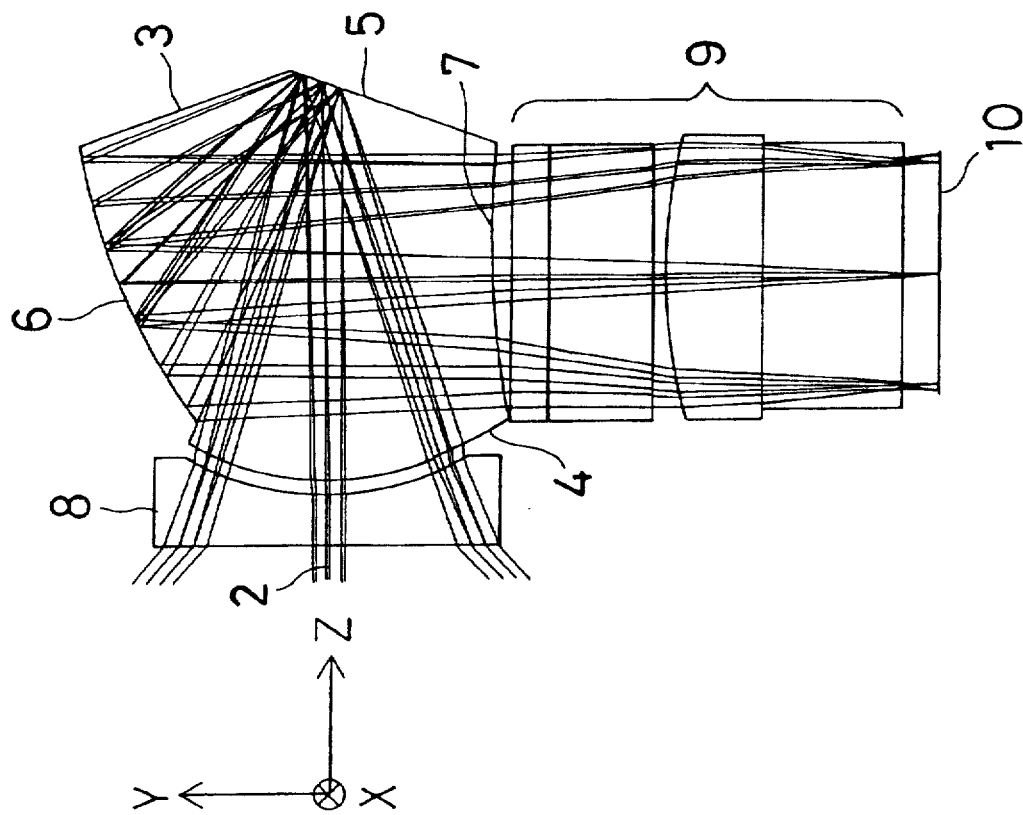
FIG. 1 is a sectional view of an endoscope optical system according to Example 1 of the present invention.

In constituent parameters of each example (described later), as shown in FIG. 1, the vertex of a first surface 4 of a prism optical system 3 is defined as the origin of the optical system in Examples 1 and 2. In Examples 3 to 5, the vertex of the object-side surface of a plano-concave lens in a first lens system 8, which is disposed on the object side of the prism optical system 3, is defined as the origin of the optical system. An optical axis 2 is defined by a light ray which emanates from the center of an object (not shown) and passes through the center of a stop to reach the center of an image plane 10. A Z-axis is taken in a direction in which light rays travel from the first transmitting surface 4 of the prism optical system 3 along the optical axis 2. A Y-axis is taken in a direction which extends through the first surface 4 of the prism optical system 3 or the object-side surface of the first lens system 8 at right angles to the Z-axis in a plane in which light rays are bent by the prism optical system 3. An X-axis is taken in a direction which extends through the first surface 4 of the prism optical system 3 or the object-side surface of the first lens system 8 at right angles to both the Z- and Y-axes. A direction in which the Z-axis extends from the object point toward the prism optical system 3 is defined as a positive direction of the Z-axis. A direction in which the Y-axis extends from the optical axis 2 away from the image plane 10 is defined as a positive direction of the Y-axis. A direction in which the X-axis constitutes a right-handed system in combination with the Z- and Y-axes is defined as a positive direction of the X-axis.

Regarding displacement and tilt of each of surfaces including a hypothetic plane, there are shown amounts of displacement in the X-, Y- and Z-axis directions from the origin of the coordinate system (Examples 1 and 2: the vertex of the first surface 4 of the prism optical system 3; Examples 3 to 5: the vertex of the object-side surface of the plano-concave lens in the first lens system 8), and an amount of rotation of the surface about the X-axis is given by α. For the tilt angle, the positive sign means the counterclockwise rotation.

Regarding the first lens system 8, which is disposed as a coaxial portion on the object side of the prism optical system 3, and the second lens system 9, which is disposed as a coaxial portion on the image side of the prism optical system 3, surface separations are given according to the conventional notation.

The configuration of each three-dimensional surface is defined by the above-described equation (a). The Z-axis of the defining equation is the axis of the three-dimensional surface. It should be noted that the term concerning an aspherical surface for which no data is shown is 0. The refractive index is expressed by the refractive index for the spectral d-line (wavelength 587.56 nanometers). Lengths are given in millimeters.

Figure 2:
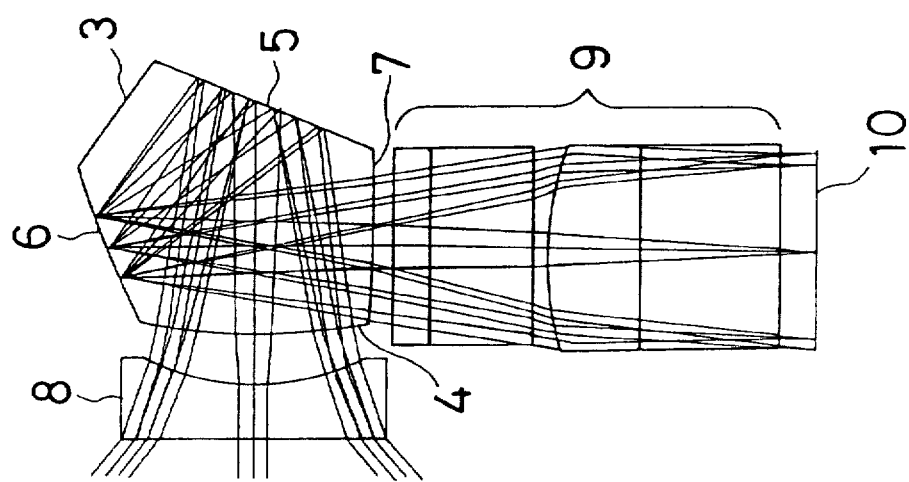
FIG. 2 is a sectional view of an endoscope optical system according to Example 2 of the present invention.
Figure 3:
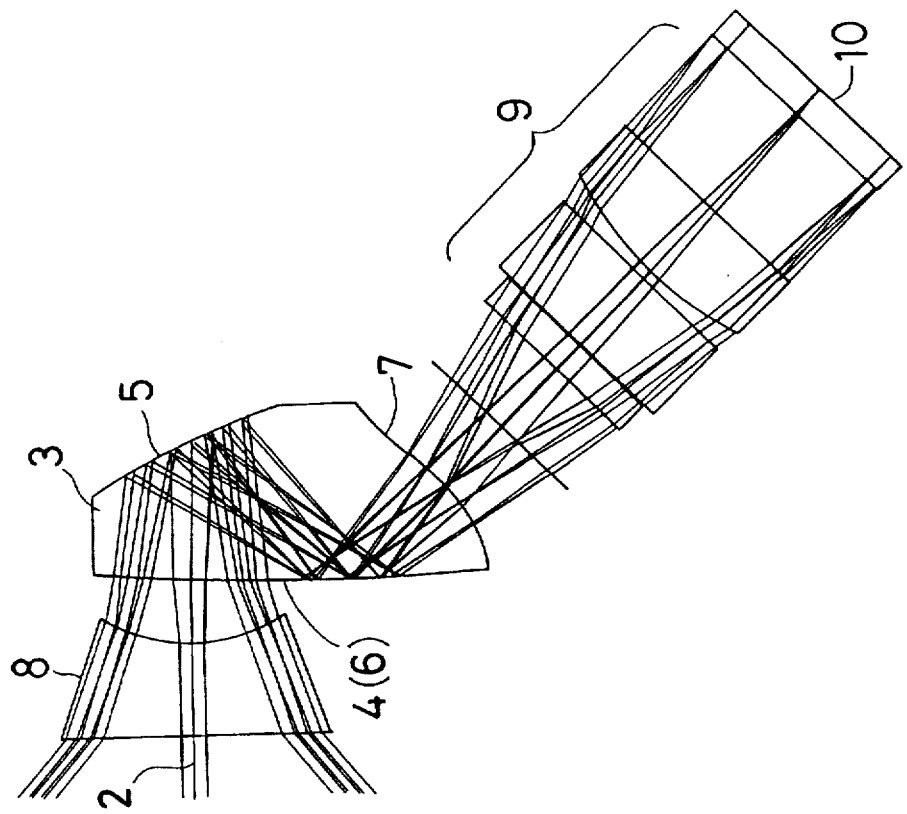
FIG. 3 is a sectional view of an endoscope optical system according to Example 3 of the present invention.
Figure 4:
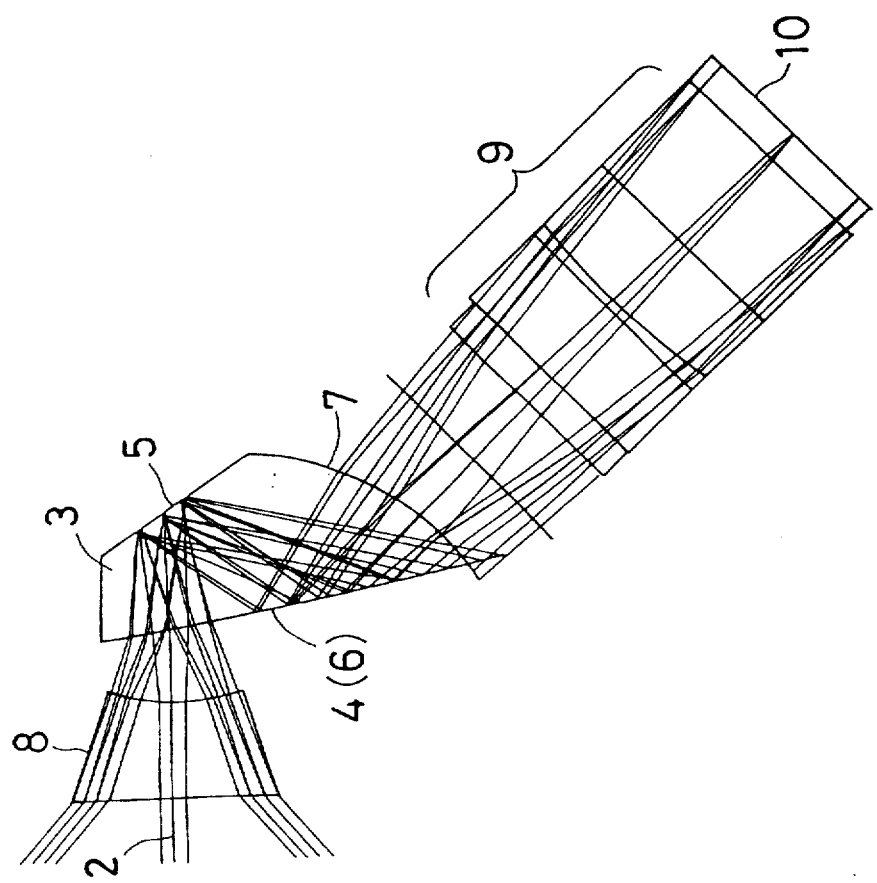
FIG. 4 is a sectional view of an endoscope optical system according to Example 4 of the present invention.
Figure 5:
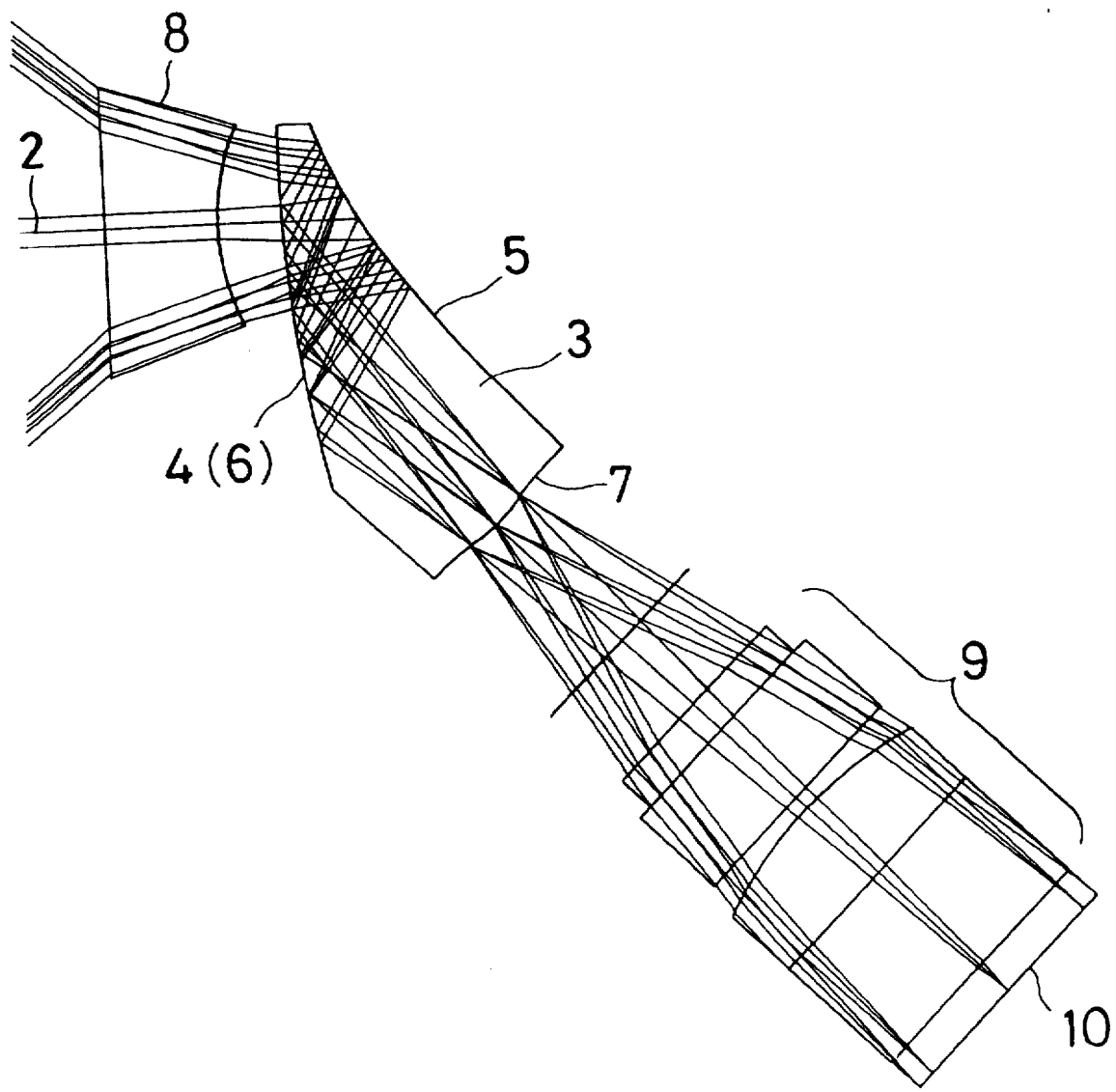
FIG. 5 is a sectional view of an endoscope optical system according to Example 5 of the present invention.
Figures 8A, 8B:
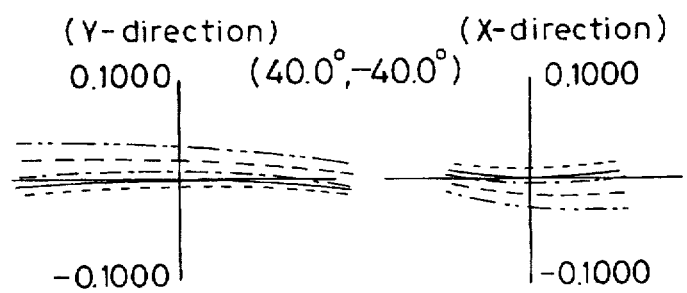
FIGS. 8A–8F are one part of an aberrational diagram illustrating lateral aberrations in the optical system according to Example 3 of the present invention.
Figures 8C, 8D:
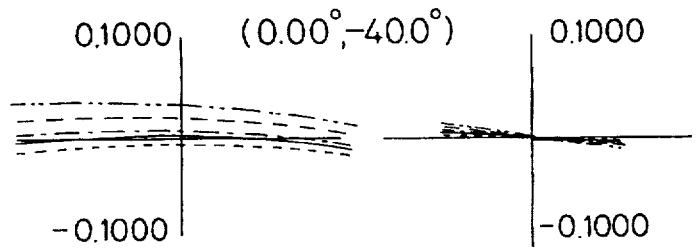
Figures 8E, 8F:
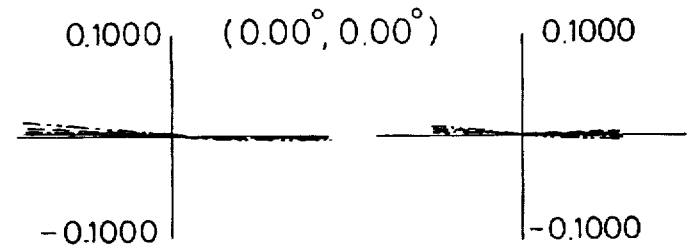
Figures 9A, 9B:
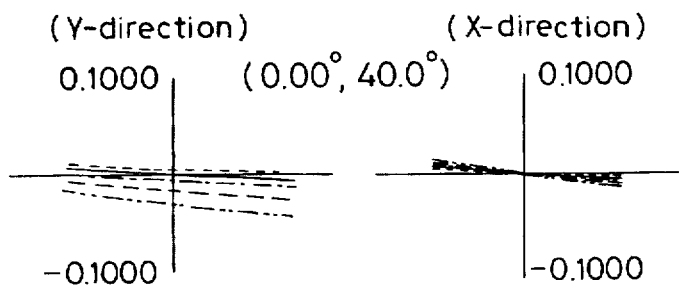
FIGS. 9A–9F are the other part of the aberrational diagram illustrating lateral aberrations in the optical system according to Example 3 of the present invention.
Figures 9C, 9D:
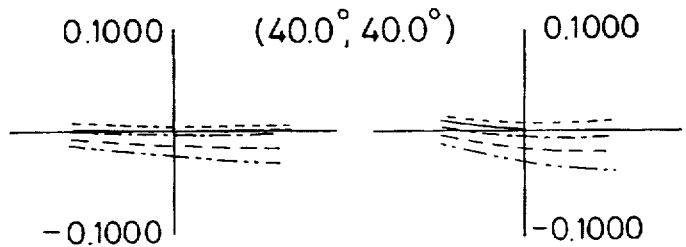
Figures 9E, 9F:
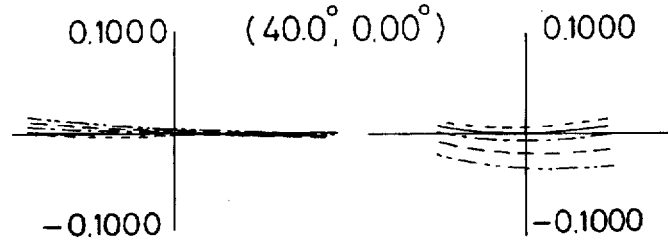
Figure 10:
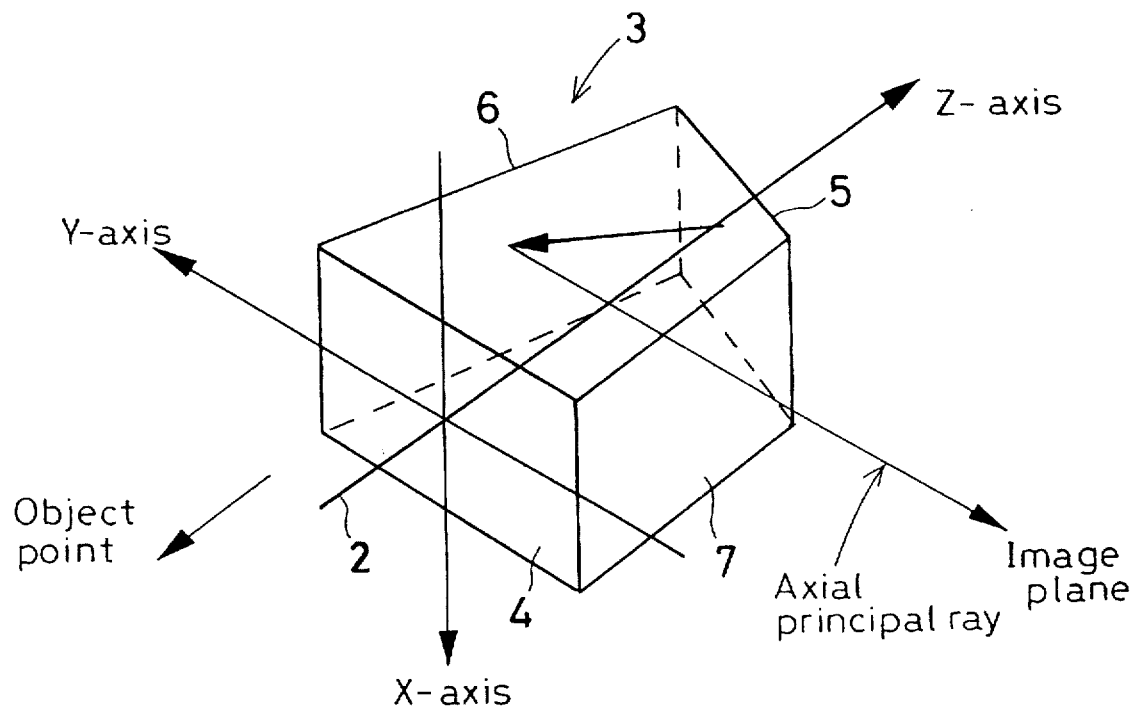
FIGS. 10(a) and 10(b) are views for describing examples of prism optical systems used in the present invention.
Figure 10:
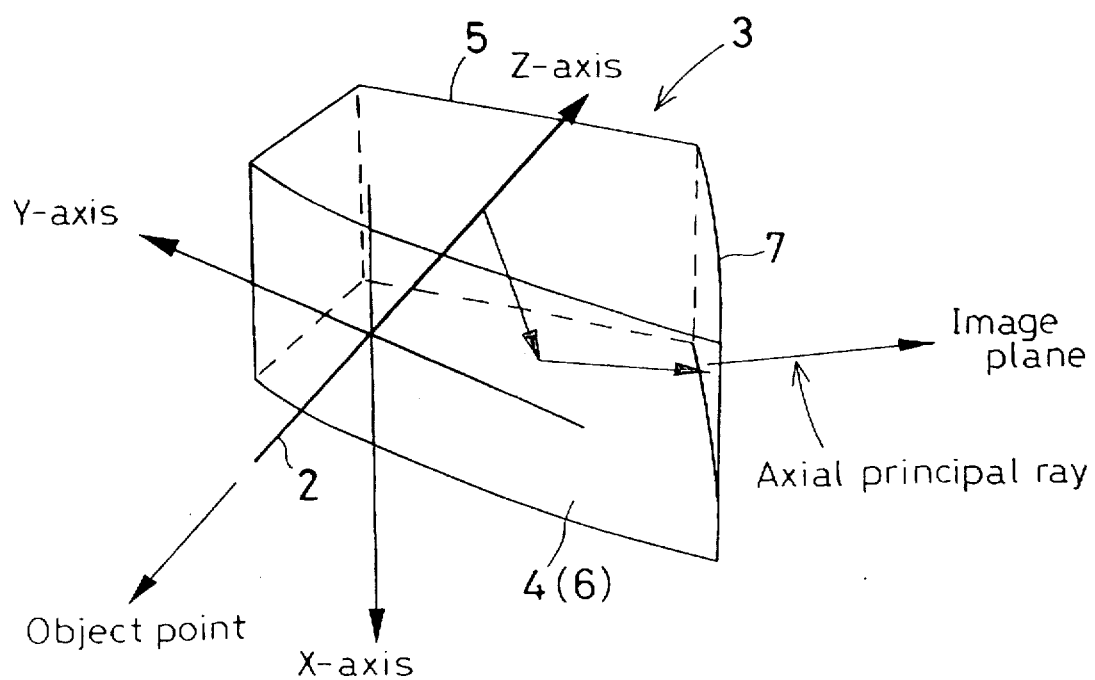

In image-forming optical systems according to Examples 1 and 2 described below, as shown in FIGS. 1 and 2, respectively, which are sectional views taken along the YZ-plane containing the optical axis 2, the first lens system 8 is disposed on the object side of the first transmitting surface 4 of the prism 3 shown in FIG. 10(a), and the second lens system 9 is disposed on the image plane side of the second transmitting surface 7 (the image plane is denoted by reference numeral 10). In image-forming optical systems according to Examples 3 to 5, as shown in FIGS. 3 to 5, respectively, which are sectional views taken along the YZ-plane containing the optical axis 2, the first lens system 8 is disposed on the object side of the first transmitting surface 4 of the prism 3 shown in FIG. 10(b), and the second lens system 9 is disposed on the image plane side of the second transmitting surface 7. It should be noted that in each prism 3 the space between the three or four surfaces is filled with a medium having a refractive index larger than 1.

Constituent parameters of Examples 1 to 5 are shown below. Regarding observation field angles, the horizontal field angle is 80°, and the vertical field angle is 80°. The object-side numerical aperture NA is 0.01349.

EXAMPLE 1

| Surface No. | Radius of curvature | Surface separation | Displacement and tilt | Refractive index | Abbe's No. |
|---|---|---|---|---|---|
| Object plane | ∞ | 11.0000 | | | |
| 1 | ∞ | 0.5000 | | 1.88300 | 40.8 |
| 2 | 2.622 | 0.2000 | | | |
| 3 | Three-dimensional surface (1) | | | 1.88300 | 40.8 |
| 4 | Three-dimensional surface (2) (Diaphragm plane) | | (1) | 1.88300 | 40.8 |
| 5 | Three-dimensional surface (3) | | (2) | 1.88300 | 40.8 |
| 6 | Three-dimensional surface (4) | | (3) | | |
| 7 | ∞ | −0.2000 | (3) | | |
| | (Hypothetic plane) | | | | |

-continued

| | | | | | |
|---|---|---|---|---|---|
| 8 | ∞ | −0.4000 | | 1.51633 | 64.1 |
| 9 | ∞ | −0.0300 | | | |
| 10 | ∞ | −1.1000 | | 1.51633 | 64.1 |
| 11 | ∞ | −0.1000 | | | |
| 12 | −5.936 | −1.0800 | | 1.72916 | 54.7 |
| 13 | ∞ | −1.9000 | | 1.51633 | 64.1 |
| Image plane | | | | | |

Three-dimensional surface (1)

| | | | | | |
|---|---|---|---|---|---|
| $C_5$ | $1.8930 \times 10^{-1}$ | $C_7$ | $-2.5307 \times 10^{-2}$ | $C_8$ | $-3.1369 \times 10^{-3}$ |
| $C_{10}$ | $-2.5730 \times 10^{-2}$ | $C_{12}$ | $2.7391 \times 10^{-4}$ | $C_{14}$ | $2.9356 \times 10^{-2}$ |
| $C_{16}$ | $4.6789 \times 10^{-3}$ | | | | |

Three-dimensional surface (2)

| | | | | | |
|---|---|---|---|---|---|
| $C_5$ | $8.2877 \times 10^{-2}$ | $C_7$ | $-2.4922 \times 10^{-2}$ | $C_8$ | $9.4201 \times 10^{-3}$ |
| $C_{10}$ | $-9.1946 \times 10^{-3}$ | $C_{12}$ | $-4.5614 \times 10^{-3}$ | $C_{14}$ | $-3.9128 \times 10^{-3}$ |
| $C_{15}$ | $-2.3717 \times 10^{-3}$ | | | | |

Three-dimensional surface (3)

| | | | | | |
|---|---|---|---|---|---|
| $C_5$ | $6.7185 \times 10^{-2}$ | $C_7$ | $2.7094 \times 10^{-2}$ | $C_8$ | $2.0355 \times 10^{-3}$ |
| $C_{10}$ | $-6.3609 \times 10^{-3}$ | $C_{12}$ | $2.9693 \times 10^{-1}$ | $C_{11}$ | $4.6964 \times 10^{-4}$ |
| $C_{15}$ | $-2.1334 \times 10^{-3}$ | | | | |

Three-dimensional surface (4)

| | | | | | |
|---|---|---|---|---|---|
| $C_5$ | $-6.6602 \times 10^{-2}$ | $C_7$ | $3.9820 \times 10^{-2}$ | $C_8$ | $-1.1674 \times 10^{-2}$ |
| $C_{10}$ | $-4.0535 \times 10^{-2}$ | $C_{12}$ | $4.3577 \times 10^{-3}$ | $C_{14}$ | $-1.6030 \times 10^{-2}$ |
| $C_{16}$ | $-3.1645 \times 10^{-3}$ | | | | |

| Displacement and tilt | X | Y | Z | α(°) |
|---|---|---|---|---|
| (1) | 0.0000 | 0.0000 | 4.4000 | −22.5000 |
| (2) | 0.0000 | 2.2000 | 2.2000 | −67.5000 |
| (3) | 0.0000 | −1.8000 | 2.2000 | 90.0000 |

EXAMPLE 2

| Surface No. | Radius of curvature | Surface separation | Displacement and tilt | Refractive index | Abbe's No. |
|---|---|---|---|---|---|
| Object plane | ∞ | 11.0000 | | | |
| 1 | ∞ | 0.5000 | | 1.88300 | 40.8 |
| 2 | 2.622 | 0.6300 | | | |
| 3 | Three-dimensional surface (1) | | | 1.88300 | 40.8 |
| 4 | Three-dimensional surface (2) | | (1) | 1.88300 | 40.8 |
| 5 | Three-dimensional surface (3) (Diaphragm plane) | | (2) | 1.88300 | 40.8 |
| 6 | Three-dimensional surface (4) | | (3) | | |
| 7 | ∞ | −0.2000 | (3) | | |
| | (Hypothetic plane) | | | | |
| 8 | ∞ | −0.4000 | | 1.51633 | 64.1 |
| 9 | ∞ | −0.0300 | | | |
| 10 | ∞ | −1.1000 | | 1.51633 | 64.1 |
| 11 | ∞ | −0.1000 | | | |
| 12 | −3.624 | −1.0800 | | 1.72916 | 54.7 |
| 13 | ∞ | −1.9000 | | 1.51633 | 64.1 |
| Image plane | | | | | |

Three-dimensional surface (1)

| | | | | | |
|---|---|---|---|---|---|
| $C_5$ | $9.6306 \times 10^{-2}$ | $C_7$ | $1.4801 \times 10^{-1}$ | $C_8$ | $-4.1654 \times 10^{-3}$ |
| $C_{10}$ | $-5.4373 \times 10^{-3}$ | $C_{12}$ | $-1.3995 \times 10^{-2}$ | $C_{14}$ | $5.7366 \times 10^{-3}$ |
| $C_{16}$ | $7.8530 \times 10^{-3}$ | | | | |

Three-dimensional surface (2)

| | | | | | |
|---|---|---|---|---|---|
| $C_5$ | $1.2050 \times 10^{-2}$ | $C_7$ | $-1.3062 \times 10^{-4}$ | $C_8$ | $6.7936 \times 10^{-1}$ |
| $C_{10}$ | $-2.9550 \times 10^{-3}$ | $C_{12}$ | $-4.7071 \times 10^{-3}$ | $C_{14}$ | $-6.8060 \times 10^{-3}$ |
| $C_{15}$ | $-3.4290 \times 10^{-3}$ | | | | |

Three-dimensional surface (3)

| | | | | | |
|---|---|---|---|---|---|
| $C_5$ | $4.2045 \times 10^{-2}$ | $C_7$ | $6.9807 \times 10^{-3}$ | $C_8$ | $2.1183 \times 10^{-4}$ |
| $C_{10}$ | $-2.1725 \times 10^{-3}$ | $C_{12}$ | $-1.4412 \times 10^{-3}$ | $C_{14}$ | $-4.2677 \times 10^{-3}$ |
| $C_{15}$ | $-4.3559 \times 10^{-3}$ | | | | |

-continued

| Three-dimensional surface (4) | | | | | |
|---|---|---|---|---|---|
| $C_5$ | $3.6200 \times 10^{-2}$ | $C_7$ | $1.6868 \times 10^{-1}$ | $C_8$ | $-8.4360 \times 10^{-3}$ |
| $C_{10}$ | $-5.1615 \times 10^{-3}$ | $C_{12}$ | $3.9109 \times 10^{-3}$ | $C_{14}$ | $-1.8629 \times 10^{-3}$ |
| $C_{16}$ | $7.0002 \times 10^{-5}$ | | | | |
| Displacement and tilt | | X | Y | Z | α(°) |
| (1) | | 0.0000 | 0.0000 | 2.6000 | −22.5000 |
| (2) | | 0.0000 | 1.6000 | 1.0000 | −67.5000 |
| (3) | | 0.0000 | −1.3000 | 1.0000 | 90.0000 |

EXAMPLE 3

| Surface No. | Radius of curvature | Surface separation | Displacement and tilt | Refractive index | Abbe's No. |
|---|---|---|---|---|---|
| Object plane | ∞ | 11.0000 | | | |
| 1 | ∞ | 1.1300 | | 1.88300 | 40.8 |
| 2 | 2.273 | | | | |
| 3 | Three-dimensional surface (1) | | (1) | 1.88300 | 40.8 |
| 4 | Three-dimensional surface (2) | | (2) | 1.88300 | 40.8 |
| 5 | Three-dimensional surface (1) (Diaphragm plane) | | (1) | 1.88300 | 40.8 |
| 6 | Three-dimensional surface (3) | | (3) | | |
| 7 | ∞ (Hypothetic plane) | 1.0000 | (4) | | |
| 8 | ∞ | 0.4000 | | 1.51633 | 64.1 |
| 9 | ∞ | 0.0300 | | | |
| 10 | ∞ | 1.1000 | | 1.51633 | 64.1 |
| 11 | ∞ | 0.1000 | | | |
| 12 | 4.962 | 1.0800 | | 1.72916 | 54.7 |
| 13 | ∞ | 1.9000 | | 1.51633 | 64.1 |
| Image plane | | | | | |

| Three-dimensional surface (1) | | | | | |
|---|---|---|---|---|---|
| $C_5$ | $6.8490 \times 10^{-3}$ | $C_7$ | $-1.2240 \times 10^{-2}$ | $C_8$ | $2.9816 \times 10^{-3}$ |
| $C_{10}$ | $6.1034 \times 10^{-3}$ | $C_{12}$ | $3.7326 \times 10^{-5}$ | $C_{14}$ | $1.0005 \times 10^{-3}$ |
| $C_{16}$ | $1.9897 \times 10^{-5}$ | | | | |
| Three-dimensional surface (2) | | | | | |
| $C_5$ | $-1.1103 \times 10^{-2}$ | $C_7$ | $-2.8369 \times 10^{-2}$ | $C_8$ | $3.4307 \times 10^{-3}$ |
| $C_{10}$ | $1.8834 \times 10^{-3}$ | $C_{12}$ | $9.6598 \times 10^{-1}$ | $C_{14}$ | $-3.6522 \times 10^{-4}$ |
| $C_{16}$ | $-1.1505 \times 10^{-4}$ | | | | |
| Three-dimensional surface (3) | | | | | |
| $C_5$ | $-1.3731 \times 10^{-1}$ | $C_7$ | $-1.7795 \times 10^{-1}$ | $C_8$ | $1.1789 \times 10^{-2}$ |
| $C_{10}$ | $1.2922 \times 10^{-2}$ | $C_{12}$ | $-3.8254 \times 10^{-3}$ | $C_{14}$ | $4.6379 \times 10^{-3}$ |
| $C_{16}$ | $8.5390 \times 10^{-4}$ | | | | |

| Displacement and tilt | X | Y | Z | α(°) |
|---|---|---|---|---|
| (1) | 0.0000 | −1.9408 | 1.9202 | 0.7008 |
| (2) | 0.0000 | −0.0334 | 3.6108 | 23.6803 |
| (3) | 0.0000 | −3.1435 | 3.0330 | −49.9759 |
| (4) | 0.0000 | −3.8248 | 3.7142 | −45.0000 |

EXAMPLE 4

| Surface No. | Radius of curvature | Surface separation | Displacement and tilt | Refractive index | Abbe's No. |
|---|---|---|---|---|---|
| Object plane | ∞ | 11.0000 | | | |
| 1 | ∞ | 1.1300 | | 1.88300 | 40.8 |
| 2 | 2.273 | | | | |
| 3 | Three-dimensional surface (1) | | (1) | 1.88300 | 40.8 |
| 4 | Three-dimensional surface (2) (Diaphragm plane) | | (2) | 1.88300 | 40.8 |

-continued

| | | | | | |
|---|---|---|---|---|---|
| 5 | Three-dimensional surface (1) | | (1) | 1.88300 | 40.8 |
| 6 | Three-dimensional surface (3) | | (3) | | |
| 7 | ∞ | 1.0000 | (4) | | |
| | (Hypothetic plane) | | | | |
| 8 | ∞ | 0.4000 | | 1.51633 | 64.1 |
| 9 | ∞ | 0.0300 | | | |
| 10 | ∞ | 1.1000 | | 1.51633 | 64.1 |
| 11 | ∞ | 0.100 | | | |
| 12 | 9.932 | 1.0800 | | 1.72916 | 54.7 |
| 13 | ∞ | 1.9000 | | 1.51633 | 64.1 |
| Image plane | | | | | |

Three-dimensional surface (1)

| | | | | | |
|---|---|---|---|---|---|
| $C_5$ | $5.0123 \times 10^{-3}$ | $C_7$ | $-1.1769 \times 10^{-2}$ | $C_8$ | $3.7977 \times 10^{-4}$ |
| $C_{10}$ | $5.0134 \times 10^{-4}$ | $C_{12}$ | $3.0325 \times 10^{-5}$ | $C_{14}$ | $1.0299 \times 10^{-3}$ |
| $C_{16}$ | $-2.0092 \times 10^{-3}$ | | | | |

Three-dimensional surface (2)

| | | | | | |
|---|---|---|---|---|---|
| $C_5$ | $-7.9873 \times 10^{-3}$ | $C_7$ | $-2.3282 \times 10^{-2}$ | $C_8$ | $3.2015 \times 10^{-3}$ |
| $C_{10}$ | $1.5537 \times 10^{-3}$ | | | | |

Three-dimensional surface (3)

| | | | | | |
|---|---|---|---|---|---|
| $C_5$ | $-1.6627 \times 10^{-1}$ | $C_7$ | $-2.0353 \times 10^{-1}$ | $C_8$ | $-7.6074 \times 10^{-3}$ |
| $C_{10}$ | $3.9066 \times 10^{-3}$ | $C_{12}$ | $2.0047 \times 10^{-3}$ | $C_{14}$ | $3.8586 \times 10^{-3}$ |
| $C_{16}$ | $-4.8088 \times 10^{-3}$ | | | | |

| Displacement and tilt | X | Y | Z | α(°) |
|---|---|---|---|---|
| (1) | 0.0000 | -2.1183 | 2.5226 | 11.5848 |
| (2) | 0.0000 | 0.1082 | 3.5000 | 35.3828 |
| (3) | 0.0000 | -3.0522 | 3.5197 | -40.8095 |
| (4) | 0.0000 | -3.6724 | 4.1398 | -45.0000 |

EXAMPLE 5

| Surface No. | Radius of curvature | Surface separation | Displacement and tilt | Refractive index | Abbe's No. |
|---|---|---|---|---|---|
| Object plane | ∞ | 11.0000 | | | |
| 1 | ∞ | 1.130 | | 1.8830 | 40.78 |
| 2 | 2.273 | | | | |
| 3 | Three-dimensional surface (1) | | (1) | 1.8061 | 40.95 |
| 4 | Three-dimensional surface (2) | | (2) | 1.8061 | 40.95 |
| 5 | Three-diinensional surface (1) | | (1) | 1.8061 | 40.95 |
| 6 | Three-dimensional surface (3) | | (3) | | |
| | (Diaphragm plane) | | | | |
| 7 | ∞ | 1.000 | (4) | | |
| | (Hypothetic plane) | | | | |
| 8 | ∞ | 0.400 | | 1.5163 | 64.15 |
| 9 | ∞ | 0.030 | | | |
| 10 | ∞ | 1.100 | | 1.5163 | 64.15 |
| 11 | ∞ | 0.100 | | | |
| 12 | 4.776 | 1.080 | | 1.7292 | 54.68 |
| 13˙1 | ∞ | 1.900 | | 1.5163 | 64.15 |
| Image plane | | | | | |

Three-dimensional surface (1)

| | | | | | |
|---|---|---|---|---|---|
| $C_5$ | $2.2791 \times 10^{-2}$ | $C_7$ | $-5.7060 \times 10^{-3}$ | $C_8$ | $1.3787 \times 10^{-3}$ |
| $C_{10}$ | $3.2540 \times 10^{-3}$ | $C_{12}$ | $6.0388 \times 10^{-1}$ | $C_{14}$ | $2.5853 \times 10^{-3}$ |
| $C_{16}$ | $-6.5015 \times 10^{-4}$ | | | | |

Three-dimensional surface (2)

| | | | | | |
|---|---|---|---|---|---|
| $C_5$ | $3.0086 \times 10^{-2}$ | $C_7$ | $-1.2604 \times 10^{-2}$ | $C_8$ | $6.9673 \times 10^{-3}$ |
| $C_{10}$ | $4.5508 \times 10^{-3}$ | $C_{12}$ | $4.6048 \times 10^{-3}$ | $C_{14}$ | $1.0177 \times 10^{-2}$ |
| $C_{15}$ | $2.7656 \times 10^{-3}$ | | | | |

Three-dimensional surface (3)

| | | | | | |
|---|---|---|---|---|---|
| $C_5$ | $-1.3766 \times 10^{-1}$ | $C_7$ | $-1.8856 \times 10^{-1}$ | $C_8$ | $-1.3375 \times 10^{-2}$ |
| $C_{10}$ | $2.6916 \times 10^{-3}$ | | | | |

-continued

| Displacement and tilt | X | Y | Z | α(°) |
|---|---|---|---|---|
| (1) | 0.000 | −1.274 | 2.024 | 7.63 |
| (2) | 0.000 | 0.024 | 2.757 | 31.10 |
| (3) | 0.000 | −3.366 | 4.094 | −45.70 |
| (4) | 0.000 | −4.735 | 5.463 | −45.00 |

Lateral aberrations in Examples 1 and 3 are graphically shown in FIGS. 6A–6F and 7A–7F and FIGS. 8A–F and 9A–F, respectively. In these aberrational diagrams, the parenthesized numerals denote (horizontal (X-direction) field angle, vertical (Y-direction) field angle), and lateral aberrations at the field angles are shown.

Values of parameters concerning the conditions (1-1) to (6-1) in each example of the present invention are shown below. It should be noted that, regarding transmitting surfaces, values corresponding to the conditions concerning reflecting surfaces are also shown.

| | | Ex. 1 | Ex. 2 | Ex. 3 | Ex. 4 | Ex. 5 |
|---|---|---|---|---|---|---|
| CX/CY | First surface | −0.1337 | −0.1337 | 0.1208 | 0.0165 | 1.8110 |
| | Second surface | −0.3007 | −0.0108 | 2.5551 | 0.0160 | 2.1298 |
| | Third surface | 0.4033 | 0.1660 | −1.7871 | 0.0100 | −1.4621 |
| | Fourth surface | −0.5979 | 4.6597 | 1.2960 | −0.3325 | 1.6185 |
| FX/FX2 | First surface | −0.170 | 1.194 | 0.019 | −0.039 | 0.179 |
| | Second surface | −0.974 | −0.006 | −1.078 | 0.875 | 0.673 |
| | Third surface | 1.059 | 0.328 | −0.465 | −0.442 | −0.387 |
| | Fourth surface | 0.267 | −1.361 | 1.161 | 1.313 | 1.033 |
| FY/FY2 | First surface | 1.234 | 0.733 | 0.161 | 0.054 | 0.099 |
| | Second surface | 3.150 | 0.535 | −0.426 | 0.303 | 0.318 |
| | Third surface | 2.553 | 1.866 | 0.263 | 0.190 | 0.266 |
| | Fourth surface | −0.434 | −0.276 | 0.903 | 1.081 | 0.642 |
| DY | First surface | −0.0242 | −0.0105 | 0.0116 | 0.0017 | 0.0147 |
| | Second surface | −0.0011 | −0.0022 | 0.0016 | −0.0002 | −0.0066 |
| | Third surface | −0.0055 | −0.0003 | 0.0016 | 0.0005 | 0.0119 |
| | Fourth surface | 0.0750 | 0.0046 | 0.0051 | 0.0054 | 0.0059 |
| CX-1 | First surface | 0.1321 | 0.0233 | −0.0386 | −0.0108 | −0.0436 |
| | Second surface | 0.0125 | 0.0056 | −0.0064 | 0.0021 | 0.0272 |
| | Third surface | 0.0794 | 0.0072 | −0.0125 | 0.0022 | −0.0879 |
| | Fourth surface | −0.2158 | −0.0149 | −0.0307 | −0.0296 | −0.0581 |
| CY-1 | First surface | 0.0232 | 0.0310 | −0.0370 | −0.0042 | −0.0228 |
| | Second surface | −0.0381 | −0.0182 | −0.0342 | 0.0131 | 0.0203 |
| | Third surface | −0.0550 | 0.0043 | −0.0182 | −0.0064 | 0.0040 |
| | Fourth surface | −0.2071 | −0.0833 | −0.0779 | 0.0566 | 0.0608 |
| 1/FX | | 0.1558 | 0.1295 | 0.1602 | 0.161975 | 0.16543 |
| 1/FY | Upper ray | 0.159717 | 0.137376 | 0.159328 | 0.15937 | 0.16408 |
| | Lower ray | 0.160745 | 0.137102 | 0.158443 | 0.162053 | 0.164553 |
| | Average | 0.160231 | 0.137239 | 0.158886 | 0.160711 | 0.164317 |
| FX | | 6.42 | 7.72 | 6.24 | 6.17 | 6.04 |
| FY | | 6.24 | 7.29 | 6.29 | 6.22 | 6.09 |

Although the image-forming optical systems in the above examples use three-dimensional surfaces defined by the above-described equation (a), curved surfaces defined by any defining equation can be used in the present invention. No matter which defining equation is used, an image-forming optical system which is extremely favorably corrected for aberrations can be obtained by satisfying any or some of the conditions shown in the present invention.

Although a decentration aberration correcting surface in the above-described examples may be provided as any of reflecting and transmitting surfaces, it is desirably provided as a reflecting surface of a prism optical system with a view to attaining a compact image-forming optical system, improving productivity and efficiently correcting aberrations. It is even more desirable to provide such an aberration correcting surface as a curved surface which produces decentration aberrations.

Although a non-rotationally symmetric surface for correcting decentration aberrations may be an anamorphic surface or a toric surface, it is preferably a three-dimensional surface defined by the above-described equation (a), which has only one plane of symmetry, from the viewpoint of increasing the degree of design freedom and efficiently correcting aberrations.

It should be noted that conditional expressions which are used in conventional non-decentered systems, e.g. those for the curvature of a surface defined on the basis of the center of a coordinate system for defining a surface in which decentration is ignored, and those for the focal length of a surface, are meaningless in a case where each surface is decentered to a considerable extent as in the present invention.

Regarding the aperture, a stop may be disposed at the aperture position. Alternatively, the aperture may be formed in a structure that cuts off light rays by using a prism frame, a ray limiting device, etc.

Examples of the present invention may be applied to endoscopes or the like. The use of the present invention makes it possible to form an optical system for an endoscope having a compact distal end portion. In this case, either an optical fiber bundle or an electronic image pickup device, e.g. a CCD, may be used as an image pickup device disposed in the image plane. The present invention can also be used as an illumination optical system.

It should be noted that the prism optical systems according to the examples of the present invention can also be used with the observation field angles displaced from those in the examples of the present invention by properly shifting the configuration of each surface of the prism optical systems.

Figure 11:
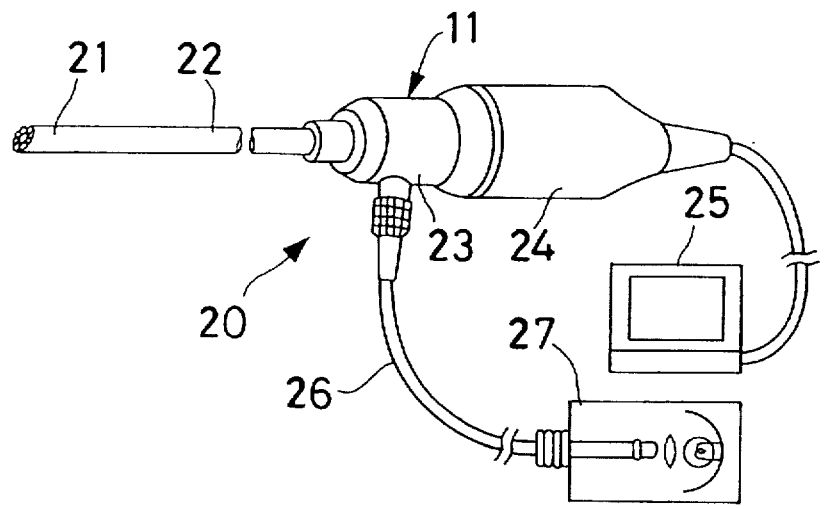
FIG. 11 shows the whole arrangement of one example of an endoscope system using an optical system according to the present invention.

The following is a description of examples of endoscopes using image-forming optical systems such as those shown in the above-described examples. FIG. 11 shows the whole arrangement of an endoscope system in which an image-forming optical system according to the present invention is used in a so-called hard endoscope. The endoscope system 20 shown in FIG. 11 includes an endoscope 11 having an insert part 22 containing an image-forming optical system and illumination optical system (not shown) according to the present invention. The endoscope system 20 further includes a camera 24, a monitor 25, and a light source unit 27.

Figure 12:
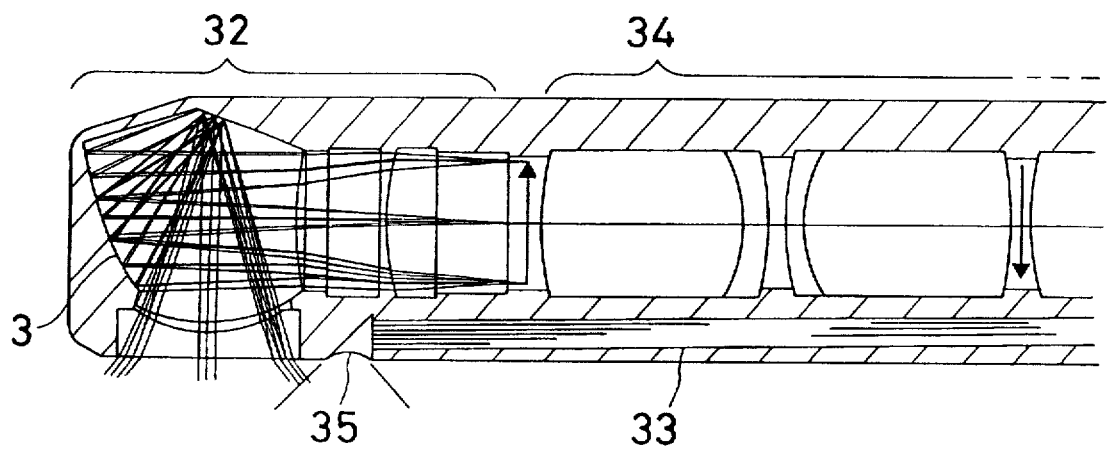
FIG. 12 is a sectional view of a distal end portion of the endoscope shown in FIG. 11.

The endoscope 11 is arranged as follows: The insert part 22 has a distal end portion 21. As shown in FIG. 12, an image-forming optical system 32, together with a light guide cable 33 for applying light in the direction of the visual field of the image-forming optical system 32, is incorporated in the distal end portion 21 of the insert part 22. In the insert part 22, a relay lens system 34, which is an image and pupil transfer optical system, is provided subsequently to the image-forming optical system 32. An ocular optical system (not shown) is disposed in a proximal portion 23 of the endoscope 11. The camera 66, which serves as an image pickup devices can be attached to the proximal portion 23 of the endoscope 11 at a position subsequent to the ocular optical system. The camera 24 is integrated with or detachably connected to the proximal portion 23 of the endoscope 11. A subject image taken by the camera 24 is eventually displayed on the monitor 25 so that it can be viewed as an endoscope image by an observer.

Illuminating light from the light source unit 27 is supplied through a light guide cable 26 and passed successively through the proximal portion 23, the insert part 22, and the distal end portion 21 to illuminate an area in the direction of the visual field.

Next, the distal end portion 21 of the endoscope will be described with reference to FIG. 12. A description of the image-forming optical system 32 is omitted because it has already been described in regard to Examples 1 to 5. An image and pupil produced by the image-forming optical system 32 are transferred toward the ocular optical system through a relay optical system 34. The arrow in FIG. 12 shows the transferred image. Then, the image is formed on the CCD (not shown) of the camera 24, which is disposed as an image pickup device at the image-formation position, and the image can be observed through the monitor 25. Although in the foregoing description, an image pickup device (e.g. an optical fiber bundle or a CCD) is disposed in the first image plane, the arrangement may be such that, as shown in FIG. 12, the first formed image is relayed through the relay optical system 34, and the above-mentioned image pickup device is disposed at the image-formation position at the rear end of the relay optical system 34. In a case where the relay optical system 34 is used, the image-forming optical system 32, including the relay optical system 34, can be regarded as an image-forming optical system according to the present invention.

Figure 13:
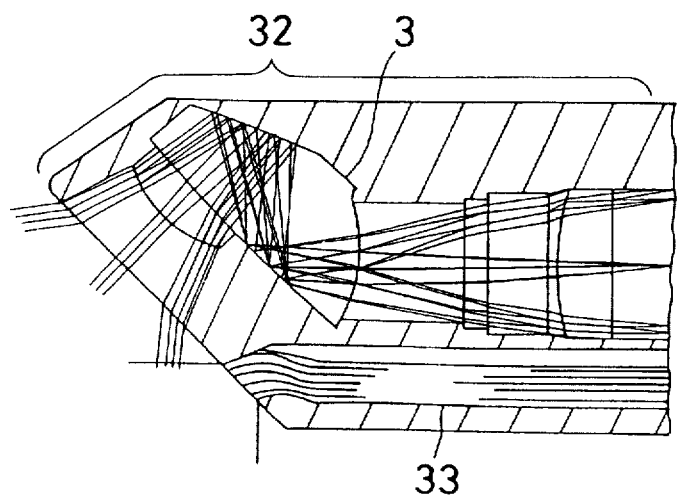
FIG. 13 is a sectional view showing a modification of the distal end portion of the endoscope.

The illumination optical system will be described below. The light guide cable (optical fiber bundle in this example) 33 inserted in the distal end portion 21 is arranged to supply light to the subject (object) side of the image-forming optical system 32. In this example, a reflecting optical element 35 having an optical power (in this example, a prism having a negative power) is disposed at the distal end of the light guide cable 33. As shown in FIG. 13, the illumination optical system may be arranged to supply light from the light guide cable 33 directly to the subject. In this way, the subject of the image-forming optical system 32 is illuminated.

Figure 14:
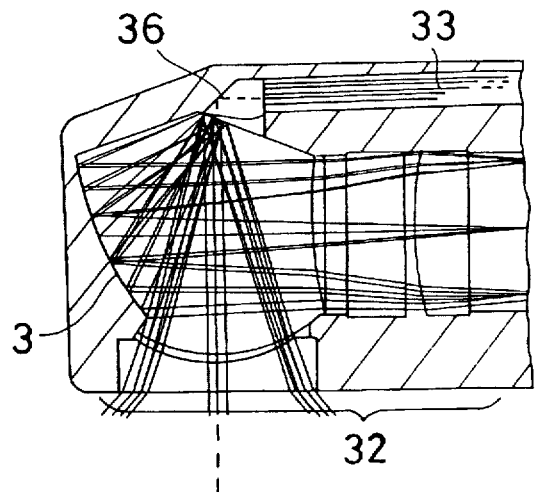
FIG. 14 is a sectional view showing a modification of an illumination system in the distal end portion of the endoscope.
Figure 15:
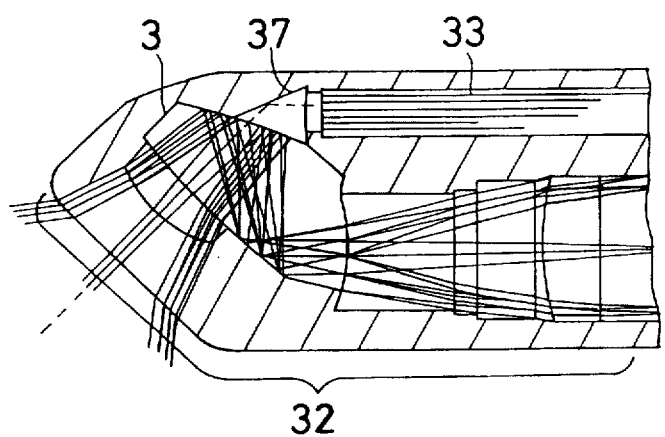
FIG. 15 is a sectional view showing another modification of the illumination system in the distal end portion of the endoscope.
Figure 16:
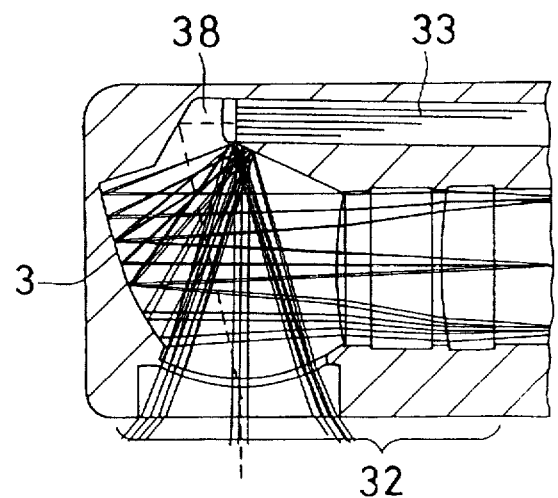
FIG. 16 is a sectional view showing still another modification of the illumination system in the distal end portion of the endoscope.

The illumination optical system may be modified as shown in FIGS. 14, 15 and 16. More specifically, illuminating light is led into the image-forming optical system 32 through a reflecting optical element (a mirror 36 in FIG. 14; a reflecting prism 37 in FIG. 15; and in FIG. 16 a reflecting surface 38 formed by deforming a part of the prism 3 in the image-forming optical system 32) which bends a bundle of light rays from the distal end of the light guide cable 33 so that the optical path of the image-forming optical system 32 and the optical path of the illumination system coincide with each other. Thus, a reflecting surface of the prism 3 in the image-forming optical system 32 may be arranged to serve as a transmitting surface of the illumination system. It is also possible to provide an illuminating light entrance surface outside the image-forming optical path of the prism 3. In this way, the subject of the image-forming optical system 32 can be illuminated favorably. In these illumination optical system arranging methods, any of the image-forming optical systems according to the present invention can be used, as required, in place of the illustrated optical systems.

Although an example that uses a relay optical system is shown in the foregoing description, an image-forming optical system may be disposed in the distal end portion of an endoscope without using a relay optical system. If an optical system according to the present invention is used as the image-forming optical system, a shortened distal end portion can be formed. This is particularly preferable in the case of an endoscope having a bendable portion for changing the direction of the optical axis of the distal end portion because the controllability of the endoscope is improved. An example of the above-described arrangement will be shown below.

Figure 17:
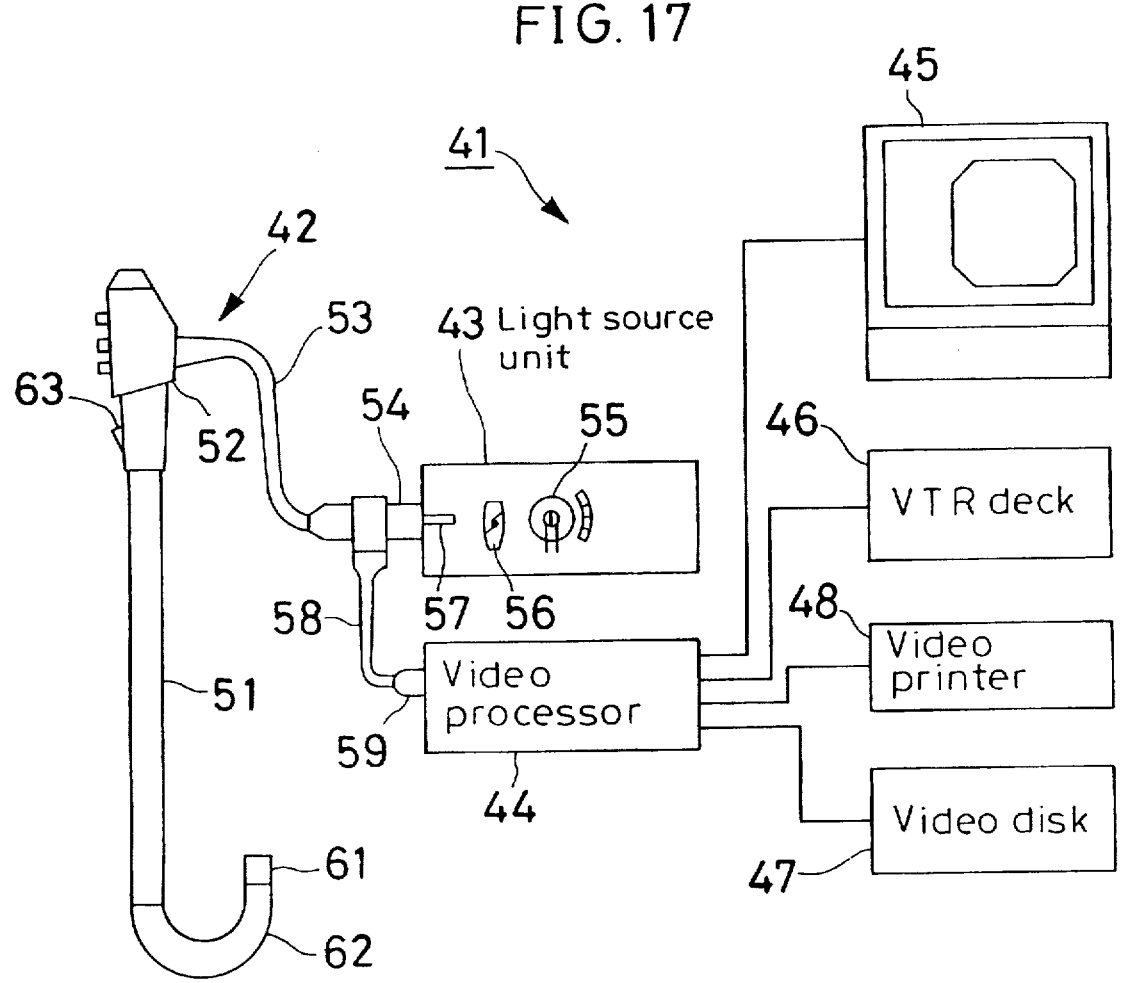
FIG. 17 shows the whole arrangement of one example of a video endoscope using an optical system according to the present invention.

FIG. 17 shows the arrangement of a video endoscope containing the above-described image-forming optical system and illumination optical system. As shown in FIG. 17, a video endoscope system 41 includes a video endoscope 42 having an image pickup device; a light source unit 43 for supplying illuminating light to the video endoscope 42; a video processor 44 for executing processing of signals associated with the video endoscope 42; a monitor 45 for displaying video signals outputted from the video processor 44; a VTR deck 46 and video disk 47 connected to the video processor 44 to record video signals and so forth; and a video printer 48 for printing out video signals in the form of images.

The video endoscope 41 has a thin insert part 51. A thick control part 52 is formed at the rear end of the insert part 51. A universal cord 53 extends from the control part 52. By connecting a connector 54 provided at the distal end of the universal cord 53 to the light source unit 43, white light from a lamp 55, which is condensed through a condenser lens 56, is supplied to the entrance end surface of a light guide 57. The connector 54 can be connected with a connector provided at one end of a signal cable 58. By connecting a connector 59 provided at the other end of the signal cable 58 to the video processor 44, an image signal captured by the video endoscope 42 is converted into a predetermined video signal by signal processing and outputted to the monitor 45, etc.

The insert part 51 has a hard distal end block 61 formed at the distal end thereof. A bendable portion 62 extends from the rear end of the distal end block 61. The bendable portion 62 can be bent horizontally and vertically by turning a bending control knob (not shown) provided on the control part 52.

A forward end portion of the distal end block 61 is provided with a forceps inlet 63 for inserting a bioptic forceps or other tool for endoscopy. The forceps inlet 63 is communicated with a forceps channel provided in the insert part 51.

Figure 18:
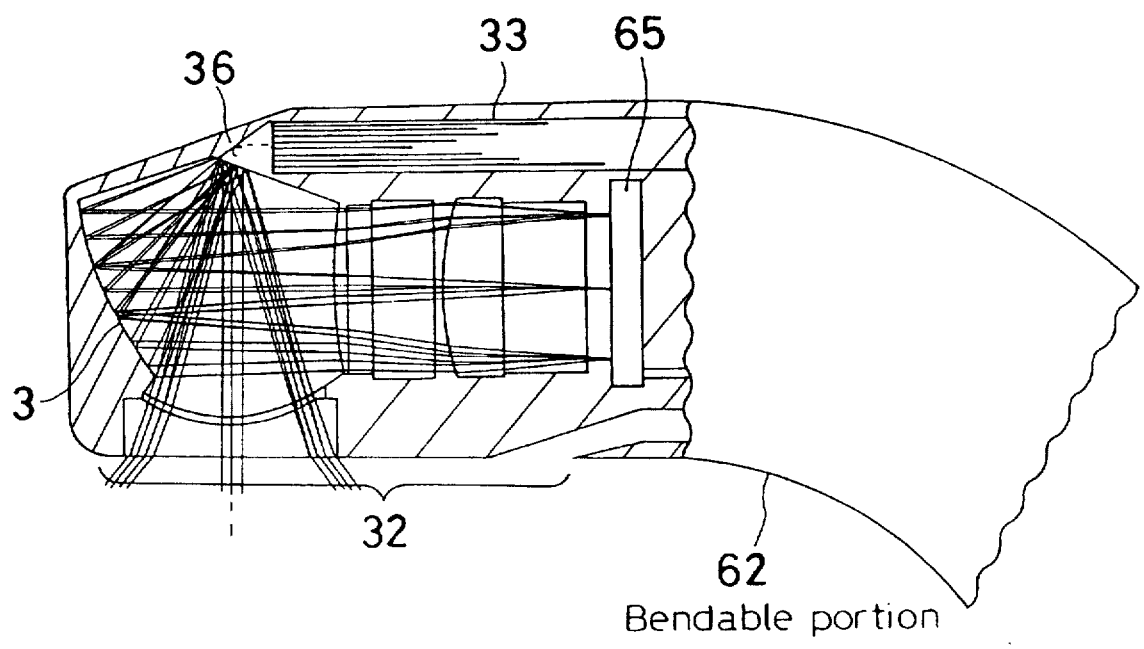
FIG. 18 is a sectional view of a distal end portion of the endoscope shown in FIG. 17.

As shown in FIG. 18, the distal end block 61 of the endoscope 42 contains the image-forming optical system 32 according to the present invention and the light guide cable 33 for illuminating an area in the direction of the visual field. As has been stated above, the distal end block 61 of the insert part 51 is provided with the optical system 32 and an image pickup device 65. The arrangement of the rest is the same as that in the above-described examples; therefore, a description thereof is omitted. It should be noted that the image-forming optical system 32 and the illumination optical system can be arranged in various forms such as those shown in FIGS. 12 to 16, as a matter of course.

As will be clear from the foregoing description, it is possible according to the present invention to provide an endoscope optical system capable of providing a clear image of minimal distortion even at a wide field angle and also provide a simple and compact objective optical system for endoscopes.

What we claim is:

1. An endoscope optical system comprising:
   an objective optical system for forming an object image, said objective optical system including a prism member having at least a reflecting surface for bending an optical path; and
   an image transfer system for leading the object image formed by said objective optical system to an observation apparatus along a direction of a major axis,
   wherein said objective optical system has a configuration that produces decentration aberration by bending the optical path; and
   wherein said prism member has at least one curved surface having an optical action in the optical path, said curved surface having no axis of rotational symmetry intersecting a surface of an area thereof where light is transmitted or reflected, said curved surface correcting said decentration aberration.

2. An endoscope optical system comprising:
   an objective optical system for forming an object image, said objective optical system including a prism member having at least a reflecting surface for bending an optical path; and
   an image transfer system for leading the object image formed by said objective optical system to an observation apparatus along a direction of a major axis;
   wherein said reflecting surface of said prism member has a surface configuration that produces decentration aberration; and
   wherein at least one of said reflecting surface and another reflecting surface of said prism member is a has no axis of rotational symmetry intersecting a surface of an area thereof where light is transmitted or reflected, said curved surface correcting said decentration aberration.

3. An endoscope optical system according to claim 1, wherein said reflecting surface of said prism member has a surface configuration that produces decentration aberration; and
   wherein said prism member has a refracting surface being a non-rotationally symmetric surface designed to correct said decentration aberration.

4. An endoscope optical system according to any one of claims 1 to 3, wherein said non-rotationally symmetric surface has only one plane of symmetry and is defined by the following equation:

$$Z = C_2 \quad (a)$$
$$+ C_3 y + C_4 x$$
$$+ C_5 y^2 + C_6 yx + C_7 x^2$$
$$+ C_8 y^3 + C_9 y^2 x + C_{10} yx^2 + C_{11} x^3$$
$$+ C_{12} y^4 + C_{13} y^3 x + C_{14} y^2 x^2 + C_{15} yx^3 + C_{16} x^4$$
$$+ C_{17} y^5 + C_{18} y^4 x + C_{19} y^3 x^2 + C_{20} y^2 x^3 + C_{21} yx^4$$
$$+ C_{22} x^5$$
$$+ C_{23} y^6 + C_{24} y^5 x + C_{25} y^4 x^2 + C_{26} y^3 x^3 + C_{27} y^2 x^4$$
$$+ C_{28} yx^5 + C_{29} x^6$$
$$+ C_{30} y^7 + C_{31} y^6 + C_{32} y^5 x^2 + C_{33} y^4 x^3 + C_{34} y^3 x^4$$
$$+ C_{35} y^2 x^5 + C_{36} yx^6 + C_{37} x^7$$

where $C_m$ (m is an integer of 2 or higher) are coefficients.

5. An endoscope optical system according to any one of claims 1 to 3, wherein said non-rotationally symmetric surface is a toric surface.

6. An endoscope optical system according to any one of claims 1 to 3, wherein said non-rotationally symmetric surface is an anamorphic surface.

7. An endoscope optical system according to any one of claims 1 to 3, wherein said prism member has at least two curved surfaces, said two curved surfaces including a first reflecting surface disposed to face an object at a tilt with respect to an optical axis, and a second reflecting surface tilted with respect to both said first reflecting surface and a plane where an image of said object is formed, at least one of said first and second reflecting surfaces being said non-rotationally symmetric surface; and wherein said prism member is arranged such that an optical axis emanating from said object is reflected by said first reflecting surface away from said plane where the image of said object is formed, and thereafter, said optical axis is reflected by said second reflecting surface toward said plane where the image of said object is formed.

8. An endoscope optical system according to claim 7, wherein said prism member is arranged such that the optical axis reflected by said second reflecting surface intersects the optical axis reflected by said first reflecting surface.

9. An endoscope optical system according to any one of claims 1 to 3, wherein said prism member has at least two curved surfaces said two curved surfaces including a first reflecting surface disposed to face an object at a tilt with respect to an optical axis, and a second reflecting surface tilted with respect to both said first reflecting surface and a plane where an image of said object is formed; and wherein said prism member is arranged such that the optical axis is reflected successively by said first and second reflecting surfaces in an N-shape.

10. An endoscope optical system according to claim 1 or 2, which satisfies the following condition:

f<20 millimeters where f is a focal length defined by a value obtained by dividing a ray height of a bundle of parallel rays incident on said objective optical system from an object side thereof by a numerical aperture at an image plane.

11. An endoscope optical system according to claim 1 or 2, wherein said objective optical system has an optical member having a power, said optical member being disposed closer to an object side than said prism member.

12. An endoscope optical system according to claim 1 or 2, wherein said objective optical system has an optical member having a power, said optical member being disposed closer to an image side than said prism member.

13. An endoscope optical system according to claim 1, 2 or 3, wherein said image transfer system has a relay optical system and an image pickup device, said image pickup device being arranged to receive a relay image transferred through said relay optical system.

14. An image pickup apparatus, comprising:

an image-forming optical system which forms an object image;

an image pickup device which receives the object image formed by said image-forming optical system; and a monitor which converts the image received by said image pickup device into an electric signal and displays an image from the electric signal;

wherein said image-forming optical system has a prism optical system in which at least one surface which transmits and/or reflects light from an object is formed from a curved surface, wherein said curved surface of said prism optical system is a non-rotationally symmetric surface, wherein said prism optical system has a prism formed from at least two curved surfaces, wherein said at least two curved surfaces include a first reflecting surface disposed at a tilt to face an object point, and a second reflecting surface tilted with respect to both said first reflecting surface and an image plane, at least one of said first and second reflecting surfaces being a non-rotationally symmetric surface having no axis of rotational symmetry, and wherein said prism optical system is arranged such that light rays from the object point travel along an optical axis and are reflected by said reflecting surface of said prism optical system toward a side opposite to the image plane with respect to the optical axis and then reflected by said second reflecting surface to reach the image plane by substantially intersecting said optical axis.

15. An image pickup apparatus, comprising:

an image-forming optical system which forms an object image;

an image pickup device which receives the object image formed by said image-forming optical system; and a monitor which converts the image received by said image pickup device into an electric signal and displays an image from the electric signal;

wherein said image-forming optical system has a prism optical system in which at least one surface which transmits and/or reflects light from an object is formed from a curved surface, wherein said curved surface of said prism optical system is a non-rotationally symmetric surface, wherein said prism optical system has a prism formed from at least two curved surfaces, wherein said at least two curved surfaces include a first reflecting surface disposed at a tilt to face an object point, and a second reflecting surface tilted with respect to both said first reflecting surface and an image plane, at least one of said first and second reflecting surfaces being a non-rotationally symmetric surface having no axis of rotational symmetry; and wherein said prism optical system is arranged such that light rays from the object point travel along an optical axis and are reflected by said first reflecting surface of said prism optical system toward the image plane with respect to the optical axis and then reflected by said second reflecting surface to reach the image plane without intersecting said optical axis.

16. An image pickup apparatus according to claim 14 or 15, wherein said image pickup apparatus satisfies the following condition:

f<20 millimeters where f is a focal length defined by a value obtained by dividing a ray height of a bundle of parallel rays incident on said image-forming optical system from an object side thereof by a numerical aperture on an image side thereof.

17. An image pickup apparatus according claim 14 or 15, wherein said image forming optical system has an optical system between the object point and said prism optical system.

18. An image pickup apparatus according to claim 14 or 15, wherein said image forming optical system has an optical system between said prism optical system and the image-formation position.

19. An endoscope optical system according to claim 1, 2 or 3, further comprising an illumination optical system which illuminates a subject of said objective optical system.

20. An image pickup apparatus according to claim 14 or 15, wherein said image forming optical system includes a relay optical system between said prism optical system and said image pickup device, so that a relay image transferred through said relay optical system is received by said image pickup device and displayed on said monitor.

21. An image pickup apparatus having an illumination optical system for illuminating a subject of the image-forming optical system of claim 14 or 15.

22. An image pickup apparatus according to claim 21, wherein illuminating light from said illumination optical system passes through said prism in said prism optical system to illuminate the subject of said image-forming optical system.

23. An image pickup apparatus according to claim 22, wherein at least one surface of said prism optical system is a transmitting and reflecting surface that reflects a bundle of light rays from said subject and transmits said illuminating light.

24. An image pickup apparatus according to claim 22, wherein an entrance surface for an optical path of said illumination optical system is formed outside an image-forming optical path in said prism.

* * * * *